(12) United States Patent
Giranda et al.

(10) Patent No.: US 7,999,117 B2
(45) Date of Patent: Aug. 16, 2011

(54) SUBSTITUTED 1H-BENZIMIDAZOLE-4-CARBOXAMIDES ARE POTENT PARP INHIBITORS

(76) Inventors: Vincent L. Giranda, Gurnee, IL (US); Thomas D. Penning, Elmhurst, IL (US); Virajkumar B. Gandhi, Gurnee, IL (US); Sheela A. Thomas, Libertyville, IL (US); Gui-Dong Zhu, Gurnee, IL (US); Jianchun Gong, Deerfield, IL (US)

( * ) Notice: Subject to any disclaimer, the term of this patent is extended or adjusted under 35 U.S.C. 154(b) by 118 days.

(21) Appl. No.: 12/413,834

(22) Filed: Mar. 30, 2009

(65) Prior Publication Data

US 2009/0186877 A1    Jul. 23, 2009

Related U.S. Application Data

(63) Continuation of application No. 11/743,200, filed on May 2, 2007, now abandoned.

(60) Provisional application No. 60/796,663, filed on May 2, 2006.

(51) Int. Cl.
*A61K 31/4184* (2006.01)
*C07D 403/10* (2006.01)

(52) U.S. Cl. ............................ 548/310.7; 514/394

(58) Field of Classification Search ............... 548/310.7
See application file for complete search history.

(56) References Cited

U.S. PATENT DOCUMENTS

| | | | |
|---|---|---|---|
| 3,864,385 A | 2/1975 | Feit et al. | |
| 4,093,726 A | 6/1978 | Winn et al. | |
| 6,372,736 B1 | 4/2002 | Kemp et al. | |
| 6,448,271 B1 | 9/2002 | Lubisch et al. | |
| 6,509,365 B1 | 1/2003 | Lubisch et al. | |
| 6,696,437 B1 | 2/2004 | Lubisch et al. | |
| 6,737,421 B1 | 5/2004 | Lubish et al. | |
| 7,166,292 B2 | 1/2007 | Isele et al. | |
| RE39,608 E | 5/2007 | Lubisch et al. | |
| 7,462,724 B2 | 12/2008 | Penning et al. | |
| 7,550,603 B2 | 6/2009 | Zhu et al. | |
| 2003/0100582 A1 | 5/2003 | Sircar et al. | |
| 2006/0229351 A1 | 10/2006 | Zhu et al. | |
| 2007/0179136 A1 | 8/2007 | Penning et al. | |
| 2007/0259937 A1 | 11/2007 | Giranda et al. | |
| 2007/0265324 A1 | 11/2007 | Wernet et al. | |
| 2008/0146638 A1 | 6/2008 | Giranda et al. | |
| 2008/0280867 A1 | 11/2008 | Giranda et al. | |
| 2008/0293795 A1 | 11/2008 | Donawho et al. | |
| 2009/0029966 A1 | 1/2009 | Donawho et al. | |
| 2009/0030016 A1 | 1/2009 | Gandhi et al. | |

FOREIGN PATENT DOCUMENTS

| | | |
|---|---|---|
| DE | 3522230 A1 | 1/1987 |
| DE | 3830060 A1 | 3/1990 |
| DE | 19916460 A1 | 10/2000 |
| DE | 10021468 A1 | 11/2001 |
| GB | 1354554 A | 5/1974 |
| WO | WO-9704771 A1 | 2/1997 |
| WO | WO-9748697 A1 | 12/1997 |
| WO | WO-9806703 A1 | 2/1998 |
| WO | WO-9833802 A1 | 8/1998 |
| WO | WO-9839343 A1 | 9/1998 |
| WO | WO-0026192 A1 | 5/2000 |
| WO | WO-0029384 A1 | 5/2000 |
| WO | WO-0032579 A1 | 6/2000 |
| WO | WO-0121615 A1 | 3/2001 |
| WO | WO-0121634 A1 | 3/2001 |
| WO | WO-0182877 A2 | 11/2001 |
| WO | WO-02068407 A1 | 9/2002 |
| WO | WO-03002698 A2 | 1/2003 |
| WO | WO-03020698 A2 | 3/2003 |
| WO | WO-03094861 A2 | 11/2003 |
| WO | WO-03106430 A1 | 12/2003 |
| WO | WO-2004054515 A2 | 7/2004 |
| WO | WO-2004065370 A1 | 8/2004 |
| WO | WO-2004096793 A1 | 11/2004 |
| WO | WO-2004098494 A2 | 11/2004 |
| WO | WO-2007041357 A1 | 4/2007 |
| WO | WO-2007059230 A3 | 5/2007 |

OTHER PUBLICATIONS

Alexy, et al., "Inhibition of ADP-Evoked Platelet Aggregation by Selected Poly(ADP-Ribose) Polymerase Inhibitors," J Cardiovasc Pharmacol, 2004, 43, pp. 423-431.*

Burkart, et al., "Mice lacking the poly (ADP-ribose) polymerase gene are resistant to pancreatic beta-cell destruction and diabetes development induced by streptozocin," Nature Medicine, 1999, 5—Issue 3, pp. 314-319.*

Chen, et al., "Potentiation of the antitumor activity of cisplatin in mice by 3-am inobenzamide and nicotinamide," Cancer Chemotherapy and Pharmacology, 1998, 22, pp. 303-307.*

(Continued)

*Primary Examiner* — Laura L. Stockton
(74) *Attorney, Agent, or Firm* — Susan L. Steele; Gregory L. Steele; Johanna M. Corbin

(57) ABSTRACT

The present invention relates to 1H-benzimidazole-4-carboxamides of formula (I),

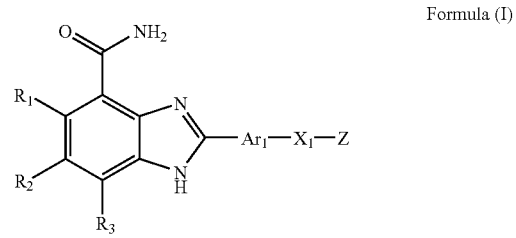

Formula (I)

their preparation, and their use as inhibitors of the enzyme poly(ADP-ribose)polymerase for the preparation of drugs.

11 Claims, No Drawings

OTHER PUBLICATIONS

Cuzzocrea, S., et al., "Protective effects of 3-aminobenzamide, an inhibitor of poly (ADP-ribose) synthase in a carrageenan-induced model of local inflammation," European Journal of Pharmacology, 1998, 342, pp. 67-76.*
Denny, et al., "Potential Antitumor Agents. 59. Structure-Activity Relationships for 2-Phenylbenzimidazole-4-carboxamides, a New Class of Minimal DNA-Intercalating Agents Which May Not Act via Topoisomerase II," J Med Chem, 1990, 33 Issue 2, pp. 814-819.*
Ehrlich, W., et al., "Inhibition of the induction of collagenase by interleukin-1β in cultured rabbit synovial fibroblasts after treatment with the poly(ADP-ribose)-polymerase inhibitor 3-aminobenzamide," Rheumatol Int, 1995, 15, pp. 171-172.*
Gilchrist et al., "Cyclisation of Ortho-Substituted N-Arylbenzimidoyl Nitrenes. Part 2.1 Preferential Cyclizations at an Ortho-Position Bearing a Methoxycarbonyl Group" J of the Chem Soci Perkin, 1979, pp. 2303-2307.*
Griffin, et al., "Novel Benzimidazole and Quinazolinone Inhibitors of the DNA Repair Enzyme Poly (ADP-ribose) polymerase," Pharmaceutical Sciences, 1996, 2 Issue 1, pp. 43-47.*
International Search Report for application No. PCT/US07/67991, Mailed on Sep. 10, 2008, 3 pages.*
IUPAC Commission on Nomenclature of Organic Chemistry: Rules for the Nomenclature of Organic Chemistry, Section E: Stereochemistry (Recommendations 1974), Pure Appl Chem, 1976, 45, 13-30.*
Kroger, H., et al., "Synergistic effects of thalidomide and poly(ADP-rose) polymerase inhibition on type Ii collagen-induced arthristis in mice," Inflammation, 1996, 20—Issue 2, pp. 203-215.*
Ohkura, et al., "Mechanism of the Color Reaction between m-Dinitrobenzene and Alkali Cyanide. II. Color Reaction Products of 2,4-Dinitroaniline with Postassium Cyanide (Organic Analysis. LXX II I)," Chem Pharm Bull, 1970, 18—Issue 11, pp. 2164-2168.
Poste et al., "Lipid Vesicles as Carriers for Introducing Biologically Active Materials into Cells," Methods in Cell Biology, 1976, 33-71, Chapter 4, vol. 14, Academic Press.
Prescott, et al., "Lipid Vesicles as Carriers for Introducing Biologically Active Materials into Cells," Methods in Cell Biology, 1976, 33-71, vol. 14, Academic Press.
Search Report No. 20030374, Jun. 13, 2003.
Search Report No. 20030487, Sep. 19, 2003.
Search Report No. 20050150, Apr. 22, 2005.
Search Report No. 20050207, May 27, 2005.
Supplementary European search report for publication No. EP2012780A2, mailed on May 11, 2009, 2 pages.
Szabo, C., et al., "Protection against peroxynitrite-induced fibroblast injury and arthritis development by inhibition of poly(ADP-ribose) synthase," Proc Natl Acad Sci USA, 1998, 95, pp. 3867-3872.
Thiemermann, C., et al., "Inhibition of the activity of poly (ADP ribose) synthetase reduces ischemia-reperfusion injury in the heart and skeletal muscle," Proc. Natal. Acad. Sci. USA, 1997, 94, pp. 679-683.
U.S. Appl. No. 09/830,992, filed May 3, 2001, inventor Wilfried Lubisch.
U.S. Appl. No. 10/935,683, filed Sep. 7, 2004, inventor Wilfried Lubisch.
U.S. Appl. No. 11/401,635, filed Apr. 11, 2006, inventor Gui-Dong Zhu.
U.S. Appl. No. 11/536,994, filed Sep. 29, 2006, inventor Thomas D. Penning.
U.S. Appl. No. 11/623,996, filed Jan. 17, 2007, inventor Wolfgang Wernet.
U.S. Appl. No. 11/743,200, filed May 2, 2007, inventor Vincent L. Giranda.
U.S. Appl. No. 11/970,828, filed Jan. 8, 2008, inventor Vincent L. Giranda.
U.S. Appl. No. 12/058,478, filed Mar. 28, 2008, inventor Vincent L. Giranda.
U.S. Appl. No. 12/116,823, filed May 7, 2008, inventor Cherrie K. Donawho.
U.S. Appl. No. 12/117,452, filed May 8, 2008, inventor Cherrie K. Donawho.
U.S. Appl. No. 12/173,213, filed Jul. 15, 2008, inventor Virajkumar B. Gandhi.
Weltin, et al., "Immunosuppressive activities of 6(5h)-phenanthridinone, a new poly (adp-ribose) polymerase inhibitor," Int J Immunopharmac., 1995, 17—Issue4, pp. 265-271.
White A.W. et al., "Potentiation of cytotoxic drug activity in human cell lines, by amine substituted 2-arylbenzimidazole-4-carboxamide PARP-1 inhibitors," Bioorganic and medicinal chemistry letters, 2004, 14 (10), pp. 2433-2437.

* cited by examiner

SUBSTITUTED 1H-BENZIMIDAZOLE-4-CARBOXAMIDES ARE POTENT PARP INHIBITORS

This application is a continuation of U.S. application Ser. No. 11/743,200, filed on May 2, 2007, abandoned, which claims priority to U.S. Provisional Application Ser. No. 60/796,663, filed May 2, 2006, both of which are herein incorporated by reference.

TECHNICAL FIELD

The present invention relates to 1H-benzimidazole-4-carboxamides, their preparation, and their use as inhibitors of the enzyme poly(ADP-ribose)polymerase for the preparation of drugs.

BACKGROUND

Poly(ADP-ribose)polymerase (PARP) or poly(ADP-ribose)synthase (PARS) has an essential role in facilitating DNA repair, controlling RNA transcription, mediating cell death, and regulating immune response. These actions make PARP inhibitors targets for a broad spectrum of disorders. PARP inhibitors have demonstrated efficacy in numerous models of disease, particularly in models of ischemia reperfusion injury, inflammatory disease, degenerative diseases, protection from adverse effects of cytoxic compounds, and the potentiation of cytotoxic cancer therapy. PARP has also been indicated in retroviral infection and thus inhibitors may have use in antiretroviral therapy. PARP inhibitors have been efficacious in preventing ischemia reperfusion injury in models of myocardial infarction, stroke, other neural trauma, organ transplantation, as well as reperfusion of the eye, kidney, gut and skeletal muscle. Inhibitors have been efficacious in inflammatory diseases such as arthritis, gout, inflammatory bowel disease, CNS inflammation such as MS and allergic encephalitis, sepsis, septic shock, hemmorhagic shock, pulmonary fibrosis, and uveitis. PARP inhibitors have also shown benefit in several models of degenerative disease including diabetes (as well as complications) and Parkinsons disease. PARP inhibitors can ameliorate the liver toxicity following acetominophen overdose, cardiac and kidney toxicities from doxorubicin and platinum based antineoplastic agents, as well as skin damage secondary to sulfur mustards. In various cancer models, PARP inhibitors have been shown to potentiate radiation and chemotherapy by increasing cell death of cancer cells, limiting tumor growth, decreasing metastasis, and prolonging the survival of tumor-bearing animals.

SUMMARY OF THE INVENTION

In one embodiment, the present invention provides compounds of Formula (I)

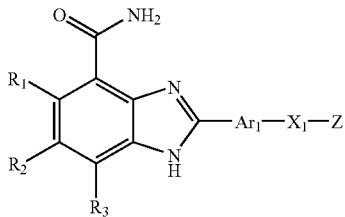

Formula (I)

or a therapeutically acceptable salt thereof, wherein
$R_1$, $R_2$, and $R_3$ are independently selected from the group consisting of hydrogen, alkenyl, alkoxy, alkoxycarbonyl, alkyl, alkynyl, cyano, haloalkoxy, haloalkyl, halogen, hydroxy, hydroxyalkyl, nitro, $NR_AR_B$, and $(NR_AR_B)$carbonyl;

$Ar_1$ is selected from the group consisting of aryl and heteroaryl, wherein $Ar_1$ is optionally substituted with 1, 2, 3, or 4 substituents selected from the group consisting of alkyl, cyano, halogen, and haloalkyl;

$X_1$ is alkylenyl;

Z is heterocycle, wherein Z is optionally substituted with 1, 2, 3, or 4 substituents selected from the group consisting of alkenyl, alkyl, alkylcarbonyl, alkylcarbonylalkyl, alkynyl, alkoxy, alkoxyalkyl alkoxycarbonyl, alkoxycarbonylalkyl, aryl, arylalkyl, carboxy, cyano, cycloalkyl, cycloalkylalkyl, cycloalkylalkoxy, cycloalkylcarbonyl, cycloalkylcarbonylalkyl, halogen, haloalkyl, heteroaryl, heteroarylalkyl, heteroarylcarbonyl, heteroarylcarbonylalkyl, heterocycle, heterocyclealkyl, heterocyclecarbonyl, heterocyclecarbonylalkyl, hydroxy, hydroxyalkyl, $NR_CR_D$, $NR_CR_D$alkyl, $(NR_CR_D)$carbonyl, $(NR_CR_D)$carbonylalkyl, and oxo;

$R_A$ and $R_B$ are independently selected from the group consisting of hydrogen, alkyl, and alkylcarbonyl, or $R_A$ and $R_B$ together with the nitrogen atom to which they are attached form a heterocycle; and $R_C$ and $R_D$ are independently selected from the group consisting of hydrogen, alkyl, alkycarbonyl, cycloalkyl, and cycloalkylalkyl.

DETAILED DESCRIPTION OF THE INVENTION

In another embodiment, the present invention provides compounds of Formula (I)

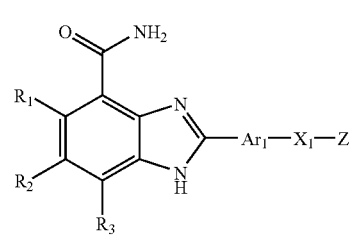

Formula (I)

or a therapeutically acceptable salt thereof, wherein
$R_1$, $R_2$, and $R_3$ are independently selected from the group consisting of hydrogen, and halogen;

$Ar_1$ is selected from the group consisting of aryl and heteroaryl, wherein $Ar_1$ is optionally substituted with halogen;

$X_1$ is alkylenyl;

Z is heterocycle, wherein Z is optionally substituted with 1, 2, 3, or 4 substituents selected from the group consisting of alkyl, alkoxy, alkoxyalkyl, haloalkyl, hydroxyalkyl, $NR_CR_D$, and $NR_CR_D$alkyl; and $R_C$ and $R_D$ are independently selected from the group consisting of hydrogen, alkyl, cycloalkyl, and cycloalkylalkyl.

In another embodiment, the present invention provides a pharmaceutical composition comprising a compound of Formula (I), wherein $Ar_1$ is phenyl.

In another embodiment, the present invention provides a pharmaceutical composition comprising a compound of Formula (I), wherein Z is pyrrolidinyl optionally substituted with 1, 2, 3, or 4 substituents selected from the group consisting of alkenyl, alkyl, alkylcarbonyl, alkylcarbonylalkyl, alkynyl, alkoxy, alkoxyalkyl alkoxycarbonyl, alkoxycarbonylalkyl, aryl, arylalkyl, carboxy, cyano, cycloalkyl, cycloalkylalkyl, halogen, haloalkyl, hydroxy, hydroxyalkyl, $NR_CR_D$, $NR_CR_D$alkyl, $(NR_CR_D)$carbonyl, $(NR_CR_D)$carbonylalkyl, and oxo; and $R_C$ and $R_D$ are independently selected from the group consisting of hydrogen, alkyl, alkycarbonyl, cycloalkyl, and cycloalkylalkyl.

In another embodiment, the present invention provides a pharmaceutical composition comprising a compound of Formula (I), wherein Z is pyrrolidinyl optionally substituted with $NR_CR_D$.

In another embodiment, the present invention provides a pharmaceutical composition comprising a compound of Formula (I), wherein Z is pyrrolidinyl optionally substituted with alkyl.

In another embodiment, the present invention provides a pharmaceutical composition comprising a compound of Formula (I), wherein Z is pyrrolidinyl optionally substituted with $NR_CR_D$alkyl.

In another embodiment, the present invention provides a pharmaceutical composition comprising a compound of Formula (I), wherein Z is pyrrolidinyl optionally substituted with hydroxyalkyl.

In another embodiment, the present invention provides a pharmaceutical composition comprising a compound of Formula (I), wherein $Ar_1$ is phenyl and Z is pyrrolidinyl.

In another embodiment, the present invention provides a pharmaceutical composition comprising a compound of Formula (I), wherein $Ar_1$ is phenyl substituted with halogen.

In another embodiment, the present invention provides a pharmaceutical composition comprising a compound of Formula (I), wherein $R_1$, $R_2$, and $R_3$ are hydrogen.

In another embodiment, the present invention provides a pharmaceutical composition comprising a compound of Formula (I), or a therapeutically acceptable salt thereof, in combination with a therapeutically acceptable carrier.

In another embodiment, the present invention provides a method of inhibiting PARP in a mammal in recognized need of such treatment comprising administering to the mammal a therapeutically acceptable amount of a compound of Formula (I) or a therapeutically acceptable salt thereof.

In another embodiment, the present invention provides a method of treating cancer in a mammal in recognized need of such treatment comprising administering to the mammal a therapeutically acceptable amount of a compound of Formula (I) or a therapeutically acceptable salt thereof.

In another embodiment, the present invention provides a method for decreasing tumor volume in a mammal in recognized need of such treatment comprising administering to the mammal a therapeutically acceptable amount of a compound of Formula (I) or a therapeutically acceptable salt thereof.

In another embodiment, the present invention provides a method of treating leukemia, colon cancer, glioblastomas, lymphomas, melanomas, carcinomas of the breast, or cervical carcinomas in a mammal in recognized need of such treatment comprising administering to the mammal a therapeutically acceptable amount of a compound of Formula (I) or a therapeutically acceptable salt thereof.

In another embodiment, the present invention provides a method of potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a method of potentiation of radiation therapy in a mammal in recognized need of such treatment comprising administering to the mammal a therapeutically acceptable amount of a compound of Formula (I) or a therapeutically acceptable salt thereof.

In another embodiment, the present invention provides a method of treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a method of reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a method of treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a method of treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a method of treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a method of treating hypoglycemia in a mammal in recognized need of such treatment comprising administering to the mammal a therapeutically acceptable amount of a compound of Formula (I) or a therapeutically acceptable salt thereof.

In another embodiment, the present invention provides a method of treating retroviral infection in a mammal in recognized need of such treatment comprising administering to the mammal a therapeutically acceptable amount of a compound of Formula (I) or a therapeutically acceptable salt thereof.

In another embodiment, the present invention provides a method of treating liver toxicity following acetominophen overdose in a mammal in recognized need of such treatment comprising administering to the mammal a therapeutically acceptable amount of a compound of Formula (I) or a therapeutically acceptable salt thereof.

In another embodiment, the present invention provides a method of treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a method of treating skin damage secondary to sulfur mustards in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for inhibiting the PARP enzyme in a mammal in recognized need of such treatment.

In another embodiment, the present invention provides a use of a compound of Formula (I), or a therapeutically acceptable salt thereof, to prepare a medicament for inhibiting tumor growth in a mammal in recognized need of such treatment.

In another embodiment, the present invention provides a use of a compound of Formula (I), or a therapeutically acceptable salt thereof, to prepare a medicament for treating cancer in a mammal in recognized need of such treatment.

In another embodiment, the present invention provides a use of a compound of Formula (I), or a therapeutically acceptable salt thereof, to prepare a medicament for treating leukemia, colon cancer, glioblastomas, lymphomas, melanomas, carcinomas of the breast, or cervical carcinomas in a mammal in a mammal in recognized need of such treatment.

In another embodiment, the present invention provides a use of a compound of Formula (I), or a therapeutically acceptable salt thereof, to prepare a medicament for potentiation of cytotoxic cancer therapy in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for potentiation of radiation in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating ischemia reperfusion injury associated with, but not limited to, myocardial infarction, stroke, other neural trauma, and organ transplantation, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating reperfusion including, but not limited to, reperfusion of the eye, kidney, gut and skeletal muscle, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating inflammatory diseases including, but not limited to, arthritis, gout, inflammatory bowel disease, CNS inflammation, multiple sclerosis, allergic encephalitis, sepsis, septic shock, hemmorhagic shock, pulmonary fibrosis, and uveitis in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating immunological diseases or disorders such as rheumatoid arthritis and septic shock in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating degenerative disease including, but not limited to, diabetes and Parkinsons disease, in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating hypoglycemia in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating retroviral infection in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating liver toxicity following acetaminophen overdose in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating cardiac and kidney toxicities from doxorubicin and platinum based antineoplastic agents in a mammal in recognized need of such treatment comprising administering to the mammal a therapeutically acceptable amount of a compound of Formula (I) or a therapeutically acceptable salt thereof.

In another embodiment, the present invention provides a use of a compound of Formula (I), or a therapeutically acceptable salt thereof, to prepare a medicament for treating skin damage secondary to sulfur mustards in a mammal in recognized need of such treatment comprising administering to the mammal a therapeutically acceptable amount of a compound of Formula (I) or a therapeutically acceptable salt thereof.

Definitions

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means at least one alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkyl group, as defined herein.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylenyl" as used herein, means a divalent group derived from a straight or branched chain hydrocarbon of from 1 to 6 carbon atoms. Representative examples include, but are not limited to, —$CH_2$—, —$CH(CH_3)$—, —$C(CH_3)_2$—, —$CH_2CH_2$—, —$CH_2CH_2CH_2CH_2$—, —$CH_2CH_2CH_2$—, —$CH_2CH(CH_3)CH_2$—.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl group or a naphthyl group.

The aryl groups of the present invention can be optionally substituted with one, two, three, four, or five substituents independently selected from the group consisting of alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —$NR_ER_F$, and ($NR_ER_F$)carbonyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, 1-methyl-3-phenylpropyl, and 2-naphth-2-ylethyl.

The term "carbonyl" as used herein, means a —C(O)— group.

The term "carboxy" as used herein, means a —$CO_2H$ group.

The term "cyano" as used herein, means a —CN group.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycloalkyl groups of the present invention are optionally substituted with 1, 2, 3, or 4 substituents selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, oxo, —$NR_ER_F$, and ($NR_ER_F$)carbonyl.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl ring or a bicyclic heteroaryl ring. The monocyclic heteroaryl ring is a 5 or 6 membered ring. The 5 membered ring has two double bonds and contains one, two, three or four heteroatoms independently selected from the group consisting of N, O, and S. The 6 membered ring has three double bonds and contains one, two, three or four heteroatoms independently selected from the group consisting of N, O, and S. The bicyclic heteroaryl ring consists of the 5 or 6 membered heteroaryl ring fused to a phenyl group or the 5 or 6 membered heteroaryl ring is fused to another 5 or 6 membered heteroaryl ring. Nitrogen heteroatoms contained within the heteroaryl may be optionally oxidized to the N-oxide. The heteroaryl is connected to the parent molecular moiety through any carbon atom contained within the heteroaryl while maintaining proper valence. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thienopyridinyl, thienyl, triazolyl, and triazinyl.

The heteroaryl groups of the present invention are substituted with 0, 1, 2, 3, or 4 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —$NR_ER_F$, and ($NR_ER_F$)carbonyl.

The term "heteroarylalkyl" as used herein, means a heteroaryl, as defined herein, appended to the parent molecular moiety through an alkyl group, as defined herein. Representative examples of heteroarylalkyl include, but are not limited to, pyridinymethyl.

The term "heterocycle" or "heterocyclic" as used herein, means a monocyclic or bicyclic heterocyclic ring. The monocyclic heterocyclic ring consists of a 3, 4, 5, 6, 7, or 8 membered ring containing at least one heteroatom independently selected from O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The bicyclic heterocyclic ring consists of a monocyclic heterocyclic ring fused to a cycloalkyl group or the monocyclic heterocyclic ring fused to a phenyl group or the monocyclic heterocyclic ring fused to another monocyclic heterocyclic ring. The heterocycle is connected to the parent molecular moiety through any carbon or nitrogen atom contained within the heterocycle while maintaining proper valence. Representative examples of heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The heterocycles of this invention are substituted with 0, 1, 2, or 3 substituents independently selected from alkenyl, alkoxy, alkoxyalkyl, alkoxycarbonyl, alkyl, alkylcarbonyl, alkylcarbonyloxy, alkylthio, alkylthioalkyl, alkynyl, carboxy, cyano, formyl, haloalkoxy, haloalkyl, halogen, hydroxy, hydroxyalkyl, mercapto, nitro, —$NR_ER_F$, and ($NR_ER_F$)carbonyl.

The term "heterocyclealkyl" as used herein, means a heterocycle, as defined herein, appended to the parent molecular moiety through an alkyl group, as defined herein.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "nitro" as used herein, means a —$NO_2$ group.

The term "nonaromatic" as used herein, means that a 4 membered nonaromatic ring contains zero double bonds, a 5 membered nonaromatic ring contains zero or one double bond, a 6, 7, or 8 membered nonaromatic ring contains zero, one, or two double bonds.

The term "$NR_AR_B$" as used herein, means two groups, $R_A$ and $R_B$, which are appended to the parent molecular moiety through a nitrogen atom.

The term "($NR_AR_B$)carbonyl" as used herein, means a $NR_AR_B$ group, as defined herein, appended to the parent molecular moiety through a carbonyl group, as defined herein. Representative examples of ($NR_AR_B$)carbonyl include, but are not limited to, aminocarbonyl, (methylamino)carbonyl, (dimethylamino)carbonyl, and (ethylmethylamino)carbonyl.

The term "$NR_CR_D$" as used herein, means two groups, $R_C$ and $R_D$, which are appended to the parent molecular moiety through a nitrogen atom.

The term "($NR_CR_D$)carbonyl" as used herein, means a $NR_CR_D$ group, as defined herein, appended to the parent molecular moiety through a carbonyl group, as defined herein. Representative examples of ($NR_CR_D$)carbonyl include, but are not limited to, aminocarbonyl, (methylamino)carbonyl, (dimethylamino)carbonyl, and (ethylmethylamino)carbonyl.

The term "($NR_CR_D$)carbonylalkyl" as used herein, means a ($NR_CR_D$)carbonyl group, as defined herein, appended to the parent molecular moiety through an alkyl group, as defined herein.

The term "($NR_CR_D$)sulfonyl" as used herein, means a $NR_CR_D$ group, as defined herein, appended to the parent molecular moiety through a sulfonyl group, as defined herein. Representative examples of ($NR_CR_D$)sulfonyl include, but are not limited to, aminosulfonyl, (methylamino)sulfonyl, (dimethylamino)sulfonyl, and (ethylmethylamino)sulfonyl.

The term "$NR_ER_F$" as used herein, means two groups, $R_E$ and $R_F$, which are appended to the parent molecular moiety through a nitrogen atom. $R_E$ and $R_F$ are each independently hydrogen, alkyl, and alkylcarbonyl. Representative examples of $NR_ER_F$ include, but are not limited to, amino, methylamino, acetylamino, and acetylmethylamino.

The term "($NR_ER_F$)carbonyl" as used herein, means a $NR_ER_F$ group, as defined herein, appended to the parent molecular moiety through a carbonyl group, as defined herein. Representative examples of ($NR_ER_F$)carbonyl include, but are not limited to, aminocarbonyl, (methylamino)carbonyl, (dimethylamino)carbonyl, and (ethylmethylamino)carbonyl.

The term "oxo" as used herein, means a =O moiety.

Compounds of the present invention can exist as stereoisomers, wherein asymmetric or chiral centers are present. Stereoisomers are designated (R) or (S) depending on the configuration of substituents around the chiral carbon atom. The terms (R) and (S) used herein are configurations as defined in IUPAC 1974 Recommendations for Section E, Fundamental Stereochemistry, Pure Appl. Chem., (1976), 45: 13-30, hereby incorporated by reference. The present invention contemplates various stereoisomers and mixtures thereof and are specifically included within the scope of this invention. Stereoisomers include enantiomers, diastereomers, and mixtures of enantiomers or diastereomers. Individual stereoisomers of compounds of the present invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Compounds of the present invention were named by ACD/ChemSketch version 5.06 (developed by Advanced Chemistry Development, Inc., Toronto, ON, Canada) or were given names which appeared to be consistent with ACD nomenclature.

Determination of Biological Activity
Inhibition of PARP

Nicotinamide[2,5',8-3H]adenine dinucleotide and strepavidin SPA beads were purchased from Amersham Biosiences (UK) Recombinant Human Poly(ADP-Ribose) Polymerase (PARP) purified from *E. coli* and 6-Biotin-17-NAD$^+$, were purchase from Trevigen, Gaithersburg, Md. NAD$^+$, Histone, aminobenzamide, 3-amino benzamide and Calf Thymus DNA (dcDNA) were purchased from Sigma, St. Louis, Mo. Stem loop oligonucleotide containing MCAT sequence was obtained from Qiagen. The oligos were dissolved to 1 mM in annealing buffer containing mM Tris HCl pH 7.5, 1 mM EDTA, and 50 mM NaCl, incubated for 5 min at 95° C., and followed by annealing at 45° C. for 45 minutes. Histone H1 (95% electrophoretically pure) was purchased from Roche, Indianapolis, Ind. Biotinylated histone H1 was prepared by treating the protein with Sulfo-NHS-LC-Biotin from Pierce Rockford, Ill. The biotinylation reaction was conducted by slowly and intermittently adding 3 equivalents of 10 mM Sulfo-NHS-LC-Biotin to 100 µM Histone H1 in phosphate-buffered saline, pH 7.5, at 4° C. with gentle vortexing over 1 min followed by subsequent 4° C. incubation for 1 hr. Streptavidin coated (FlashPlate Plus) microplates were purchased from Perkin Elmer, Boston, Mass.

PARP1 assay was conducted in PARP assay buffer containing 50 mM Tris pH 8.0, 1 mM DTT, 4 mM MgCl$_2$. PARP reactions contained 1.5 µM [$^3$H]-NAD$^+$ (1.6 uCi/mmol), 200 nM biotinylated histone H1, 200 nM slDNA, and 1 nM PARP enzyme. Auto reactions utilizing SPA bead-based detection were carried out in 100 µl volumes in white 96 well plates. Reactions were initiated by adding 50 µl of 2×NAD$^+$ substrate mixture to 50 µl of 2× enzyme mixture containing PARP and DNA. These reactions were terminated by the addition of 150 µl of 1.5 mM benzamide (~1000-fold over its IC50). 170 µl of the stopped reaction mixtures were transferred to streptavidin Flash Plates, incubated for 1 hr, and counted using a TopCount microplate scintillation counter. The $K_i$ data was determined from inhibition curves at various substrate concentrations and are shown in Table 1 for compounds of the present invention

TABLE 1

| Inhibition of PARP (nM) | | | | | | | |
|---|---|---|---|---|---|---|---|
| 12.4 | 7 | 2.6 | 12.5 | 8.8 | 43 | 27 | 19 |
| 55 | 6.3 | 1.9 | 18.4 | 43 | 31 | 13.1 | 7.6 |
| 17.8 | 13.9 | 3.5 | 14.1 | 18.1 | 22 | 13.3 | 15.6 |
| 4.8 | 3.8 | 1.5 | 20.5 | 55 | 13.3 | 10.8 | 30 |
| 25.5 | 8.1 | 3.2 | 21 | 116 | 18 | 18 | 19.1 |
| 31 | 41 | 39 | | | | | |

Cellular PARP Assay:

C41 cells were treated with a compound of the present invention for 30 minutes in 96 well plate. PARP was then activated by damaging DNA with 1 mM H$_2$O$_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-tween (0.05%) (blocking solution) for 30 minutes at room temperature. The cells were incubated with anti-PAR antibody 10H (1:50) in Blocking solution at 37° C. for 60 minutes followed by washing with PBS-Tween20 5 times, and incubation with goat anti-mouse fluorescein 5(6)-isothiocyanate-coupled antibody (1:50) and 1 µg/ml 4',6-diamidino-2-phenylindole (DAPI) in blocking solution at 37° C. for 60 minutes. After washing with PBS-Tween20 5 times, the analysis was performed using an fmax Fluorescence Microplate Reader (Molecular Devices, Sunnyvalle, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of the present invention penetrate cell membranes and inhibit PARP in intact cells. The $EC_{50s}$, for representative compounds of the present invention are provided in Table 2.

TABLE 2

| Cellular Activity $EC_{50}$ (nM) | | | | | |
|---|---|---|---|---|---|
| 0.8 | 10 | 2 | 4.4 | 34 | 12.8 |
| 1.5 | 7.9 | 54 | 9.5 | 42 | 8.7 |
| 62 | 14.3 | 8.7 | 41 | 4.2 | 9.2 |
| 0.8 | 108 | 11 | 3.2 | 111 | 51 |
| 1.1 | 2.1 | 0.8 | 3.2 | 5.7 | 2.6 |
| 19 | 0.2 | 1 | 1.7 | 93 | 0.9 |

As PARP inhibitors, the compounds of the present invention have numerous therapeutic applications related to, ischemia reperfusion injury, inflammatory diseases, degenerative diseases, protection from adverse effects of cytotoxic compounds, and potentiation of cytotoxic cancer therapy. In particular, compounds of the present invention potentiate radiation and chemotherapy by increasing cell death of cancer cells, limiting tumor growth, decreasing metastasis, and prolonging the survival of tumor-bearing mammals. Compounds of Formula (I) can treat leukemia, colon cancer, glioblastomas, lymphomas, melanomas, carcinomas of the breast, and cervical carcinomas.

Other therapeutic applications include, but are not limited to, retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemermann et al., Proc. Natl. Acad. Sci. USA 94 (1997), 679-683 D. Weltin et al. Int. J. Immunopharmacol. 17 (1995), 265-271; H. Kröger et al. Inflammation 20 (1996), 203-215; W. Ehrlich et al. Rheumatol. Int. 15 (1995), 171-172; C. Szabo et al., Proc. Natl. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

When used in the above or other treatments, a therapeutically effective amount of one of the compounds of the present invention can be employed as a zwitterion or as a pharmaceutically acceptable salt. By a "therapeutically effective amount" of the compound of the invention is meant a sufficient amount of the compound to treat or prevent a disease or disorder ameliorated by a PARP inhibitor at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved.

By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. The salts can be prepared in situ during the final isolation and purification of the compounds of the present invention or separately by reacting the free base of a compound of the present invention with a suitable acid. Representative acids include, but are not limited to acetic, citric, aspartic, benzoic, benzenesulfonic, butyric, fumaric, hydrochloric, hydrobromic, hydroiodic, lactic, maleic, methanesulfonic, pamoic, pectinic, pivalic, propionic, succinic, tartaric, phosphic, glutamic, and p-toluenesulfonic. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained.

A compound of the present invention may be administered as a pharmaceutical composition containing a compound of the present invention in combination with one or more pharmaceutically acceptable excipients. A pharmaceutically acceptable carrier or excipient refers to a non-toxic solid, semi-solid or liquid filler, diluent, encapsulating material or formulation auxiliary of any type. The compositions can be administered parenterally, intracisternally, intravaginally, intraperitoneally, topically (as by powders, ointments, drops or transdermal patch), rectally, or bucally. The term "parenteral" as used herein refers to modes of administration which include intravenous, intramuscular, intraperitoneal, intrasternal, subcutaneous and intraarticular injection and infusion.

Pharmaceutical compositions for parenteral injection comprise pharmaceutically-acceptable sterile aqueous or non-aqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity may be maintained, for example, by the use of coating materials such as lecithin, by the maintenance of the required particle size in the case of dispersions, and by the use of surfactants.

These compositions can also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption, such as aluminum monostearate and gelatin.

Compounds of the present invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically-acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

Total daily dose of the compositions of the invention to be administered to a human or other mammal host in single or divided doses may be in amounts, for example, from 0.0001 to 300 mg/kg body weight daily and more usually 1 to 300 mg/kg body weight. The dose, from 0.0001 to 300 mg/kg body, may be given twice a day.

Abbreviations which have been used in the descriptions of the examples that follow are: DBU for 1,8-diazabicyclo [5.4.0]undec-7-ene; DMF for N,N-dimethylformamide; DMSO for dimethylsulfoxide; $Et_2O$ for diethyl ether; EtOAc for ethyl acetate; EtOH for ethanol; HPLC for high pressure liquid chromatography; LDA for lithium diisopropylamide; MeOH for methanol; psi for pounds per square inch; TFA for trifluoroacetic acid; THF for tetrahydrofuran, and TMS for trimethylsilane.

Compounds having formula I may be made by synthetic chemical processes, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary.

Scheme 1

Compounds of formula 7 wherein $X_1$ and $Ar_1$ are as defined in formula (I), can be prepared from compounds of formula 1 as shown in Scheme 1.

A benzaldehyde or thiophene carboxaldehyde, containing a ketone or aldehyde or ketal or acetal (as appropriate), can be coupled with a compounds of formula 1 using, for example, Pd/C or sodium bisulfite, with heating, to give compounds of formula 4 (or 5 if starting with a ketone or aldehyde). Alternately, a benzoic acid or thiophene carboxylic acid, containing a ketone or aldehyde or ketal or acetal, can be coupled with 1 using standard amide forming reagents, such as 1,1'-carbonyldiimidazole (CDI), to give an intermediate amide, which can be treated with acid, such as acetic acid, with heating, to provide the benzimidazole 4 (or 5 if starting with a ketone or aldehyde). The ketal or acetal (if present) can be hydrolysed under acid-catalyzed conditions to give compounds of formula 5, which can undergo reductive amination using a cyclic amine (compounds of formula 6) to provide compounds of formula 7.

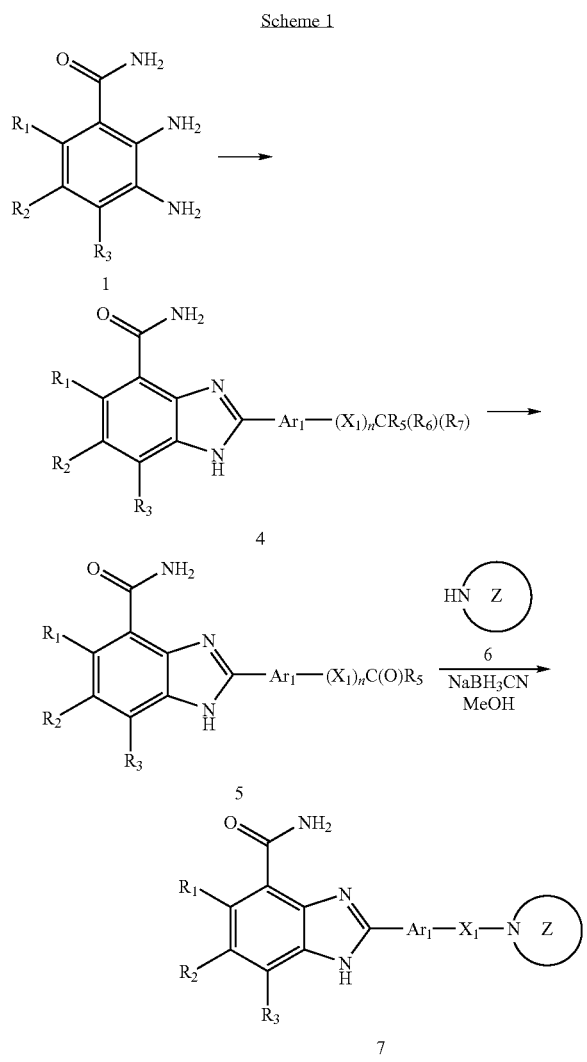

$R_6 + R_7 = OCH_2CH_2O$ or $= O$ or each OMe or OEt
$n = 0-4$

Scheme 2

Compounds of formula 12 can be prepared from compounds of formula 8 as shown in Scheme 2.

Cyclic amines can be added to compounds of formula 8 to give amides of formula 9. Compounds of formula 9 may be treated with an alkyl Grignard reagent in the presence of a catalyst such as zirconium chloride to provide compounds of formula 10. Compounds of formula 10 may undergo a lithium-halogen exchange of the aryl bromide with an alkyl lithium reagent such as sec-butyl lithium, followed by reaction with N,N'-dimethylformamide (DMF), to provide compounds of formula II. Compounds of formula II can be coupled with compounds of formula 1 using, for example, Pd/C or sodium bisulfite, with heating, to give the compounds of formula 12.

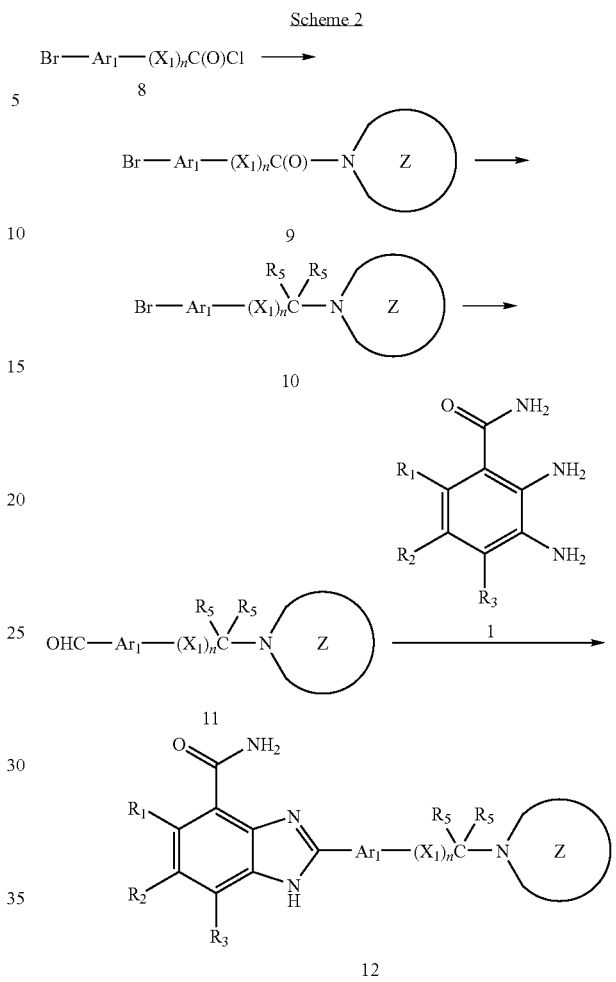

The following Examples are intended as an illustration of and not a limitation upon the scope of the invention as defined in the appended claims. The compounds of this invention can be prepared by a variety of synthetic routes.

Example 1

6-fluoro-2-[4-(2-methylpyrrolidin-1-ylmethyl)phenyl]-1H-benzimidazole-4-carboxamide Example 1A 2-bromo-4-fluoro-6-nitrophenylamine To a solution of 4-fluoro-2-nitroaniline (19.76 g, 126 mmol) in a mixture of dichloromethane (600 mL) and acetic acid (200 mL) was slowly added bromine (15 mL) at 0° C. The reaction mixture was stirred at 0° C. for 1 hour and at ambient temperature for 20 hrs. The mixture was concentrated and the residue partitioned between ethyl acetate and sodium bicarbonate solution. The organic phase was separated, washed with sodium bisulphite solution and concentrated. The residue was recrystallized from hexanes containing some dichloromethane to provide 22.7 g (76%) of the title compound. MS (DCI/NH$_3$) m/z 236 (M+H)$^+$.

Example 1B

2-amino-5-fluoro-3-nitrobenzonitrile

To a flask containing EXAMPLE 1A (6.5 g, 27.6 mmol), zinc cyanide (6.5 g, 55.3 mmol) and palladium tetrakis(triphenylphosphine) (1.6 g, 1.38 mmol) was added anhydrous N,N-dimethylformamide (120 mL) and the solution was stirred under nitrogen at 80° C. for 22 hours. After cooling, the mixture was partitioned between ethyl acetate and brine. The organic phase was washed with water and filtered. The filtrate was concentrated and the crude product recrystallized from methanol to provide 3.3 g (65%) of the title compound. MS (DCI/NH$_3$) m/z 182 (M+H)$^+$.

Example 1C

2-amino-5-fluoro-3-nitrobenzamide

A mixture of EXAMPLE 1B (3.3 g, 18.22 mmol) in polyphosphoric acid (30 g) was stirred at 115° C. for 3 hours. After cooling, water and dichloromethane were added and the precipitated solid collected by filtration and recrystallized from methanol to provide 2.6 g (72%) of the title compound. MS (DCI/NH$_3$) m/z 200 (M+H).

Example 1D

2,3-diamino-5-fluorobenzamide

To a solution of EXAMPLE 1C (1.5 g, 7.5 mmol) in 1:1 tetrahydrofuran/ethanol (100 mL) was added Raney nickel (50% in water, 1.0 g) and the mixture stirred under hydrogen (60 psi) at ambient temperature for 16 hours. The solid material was filtered off and the filtrate concentrated to provide 1.26 g (98%) of the title compound. MS (DCI/NH$_3$) m/z 170 (M+H)$^+$.

Example 1E

2-(4-diethoxymethylphenyl)-6-fluoro-1H-benzimidazole-4-carboxamide

A suspension of EXAMPLE 1D (1.5 g, 8.87 mmol) in dimethylacetamide (20 mL) was stirred for 20 minutes at 50° C. After partial cooling, terephthaldehyde mono(diethylacetal) (2.0 g, 9.76 mmol) in dimethylacetamide (5 mL) and sodium bisulphite (1.85 g, 17.74 mmol) were added and the mixture heated at 100° C. for 3 hours. After cooling to ambient temperature, the solvent was removed. The residue was partitioned between ethyl acetate and water, and the organic layer washed with brine and concentrated. The residue was purified by flash chromatography on silica gel using ethyl acetate to provide 2.4 g (63%) of the title compound. MS (DCI/NH$_3$) m/z 358 (M+H)$^+$.

Example 1F

6-fluoro-2-(4-formylphenyl)-1H-benzimidazole-4-carboxamide

To a suspension of EXAMPLE 1E in a mixture of ethanol (40 mL) and water (40 mL) was added concentrated sulfuric acid (1.5 mL) and the mixture refluxed for 18 hours. After cooling, ethanol was removed and the residue neutralized with aqueous sodium hydroxide solution and saturated sodium bicarbonate solution. The green solid was collected by filtration, washed with water and hot methanol and dried to provide 1.4 g (88%) of the title compound. MS (DCI/NH$_3$) m/z 284 (M+H)$^+$.

Example 1G

6-fluoro-2-[4-(2-methylpyrrolidin-1-ylmethyl)phenyl]-1H-benzimidazole-4-carboxamide Step A A solution of EXAMPLE 1F (60 mg, 0.21 mmol) and 2-methylpyrrolidine (36 mg, 0.42 mmol) in 1:1 methanol/N,N-dimethylformamide (5 mL) was stirred at ambient temperature for 2 hours. Sodium cyanoborohydride (27 mg, 0.42 mmol), zinc chloride (29 mg, 0.21 mmol) and dimethyl sulfoxide (1 mL) were added and the cloudy mixture stirred at 50° C. for 16 hours. The mixture was concentrated and the residue purified by HPLC (Zorbax C-8, 0.1% trifluoroacetic acid/acetonitrile/water) to provide the title compound as the trifluoroacetic acid salt.

Step B

The trifluoroacetic acid salt from step A was converted to the hydrochloride salt by dissolving in methanol and treating with anhydrous hydrogen chloride in diethyl ether to provide 20 mg (27%) of the title compound as the hydrochloride salt. $^1$H NMR (CD$_3$OD): δ 1.50 (d, J=6.7 Hz, 3H), 1.78-1.89 (m, 1H), 1.99-2.09 (m, 1H), 2.10-2.21 (m, 1H), 2.36-2.48 (m, 1H), 3.32-3.37 (m, 1H), 3.40-3.50 (m, 1H), 3.62-3.74 (m, 1H), 4.36 (d, J=13.1 Hz, 1H), 4.76 (d, J=13.1 Hz, 1H), 7.78 (dd, J=7.6, 2.1 Hz, 1H), 7.91 (dd, J=9.9, 2.3 Hz, 1H), 7.94 (d, J=8.2 Hz, 2H), 8.28 (d, J=8.2 Hz, 2H).

Example 2

6-fluoro-2-[4-((S)-2-hydroxymethylpyrrolidin-1-ylmethyl)phenyl]-1H-benzimidazole-4-carboxamide The title compound was prepared as the trifluoroacetic acid salt using the procedure as described in step A of EXAMPLE 1G, substituting (S)-(−)-pyrrolidin-2-ylmethanol for 2-methylpyrrolidine (41% yield). $^1$H NMR (CD$_3$OD): δ 1.88-2.04 (m, 2H), 2.10-2.20 (m, 1H), 2.24-2.34 (m, 1H), 3.31-3.37 (m, 1H), 3.41-3.49 (m, 1H), 3.70-3.79 (m, 2H), 3.81-3.86 (m, 1H), 4.35 (d, J=12.8 Hz, 1H), 4.75 (d, J=13.1 Hz, 1H), 7.49 (dd, J=8.1, 2.59 Hz, 1H), 7.70 (dd, J=10.4, 2.4 Hz, 1H), 7.74 (d, J=8.2 Hz, 2H), 8.29 (d, J=8.2 Hz, 2H).

Example 3

6-fluoro-2-[4-(2-trifluoromethylpyrrolidin-1-ylmethyl)phenyl]-1H-benzimidazole-4-carboxamide The title compound was prepared as the trifluoroacetic acid salt using the procedure as described in step A of EXAMPLE 1G, substituting 2-(trifluoromethyl)pyrrolidine for 2-methylpyrrolidine (34% yield). $^1$H NMR (CD$_3$OD): δ 1.84-1.96 (m, 2H), 1.99-2.09 (m, 1H), 2.15-2.27 (m, 1H), 2.62-2.70 (m, 1H), 3.05-3.14 (m, 1H), 3.62-3.72 (m, 1H), 3.91-3.99 (m, 1H), 4.35 (d, J=14.0 Hz, 1H), 7.58 (dd, J=7.9, 2.4 Hz, 1H), 7.65 (d, J=8.2 Hz, 2H), 7.77 (dd, J=10.1, 2.4 Hz, 1H), 8.15 (d, J=8.5 Hz, 2H).

Example 4

2-[4-(2-ethylpyrrolidin-1-ylmethyl)phenyl]-6-fluoro-1H-benzimidazole-4-carboxamide The title compound was prepared as the hydrochloride salt using the procedure as described in EXAMPLE 1G, substituting 2-ethylpyrrolidine for 2-methylpyrrolidine (32% yield).

¹H NMR (CD₃OD): δ 1.03 (t, J=6.0 Hz, 3H), 1.69-1.76 (m, 1H), 1.83-1.88 (m, 1H), 1.95-2.11 (m, 2H), 2.14-2.22 (m, 1H), 2.41-2.48 (m, 1H), 3.33-3.37 (m, 1H), 3.42-3.50 (m, 1H), 3.51-3.58 (m, 1H), 4.38-4.45 (m, 1H), 4.73-4.81 (m 1H), 7.81 (d, J=6.7 Hz, 1H), 7.93 (d, J=9.8 Hz, 1H), 7.98 (d, J=8.2 Hz, 2H), 8.29 (d, J=8.2 Hz, 2H).

Example 5

6-fluoro-2-[4-(2-isopropylpyrrolidin-1-ylmethyl) phenyl]-1H-benzimidazole-4-carboxamide The title compound was prepared as the trifluoroacetic acid salt using the procedure as described in step A of EXAMPLE 1G, substituting 2-isopropylpyrrolidine for 2-methylpyrrolidine (57% yield). ¹H NMR (CD₃OD): δ 1.06 (dd, J=19.5, 6.7 Hz, 6H), 1.90-2.04 (m, 2H), 2.06-2.21 (m, 2H), 2.22-2.31 (m, 1H), 3.34-3.41 (m, 1H), 3.41-3.48 (m, 1H), 3.50-3.58 (m, 1H), 4.35 (d, J=13.1 Hz, 1H), 4.63 (d, J=13.1 Hz, 1H), 7.50 (dd, J=8.2, 2.44 Hz, 1H), 7.70 (dd, J=10.4, 2.4 Hz, 1H), 7.76 (d, J=8.2 Hz, 2H), 8.29 (d, J=8.2 Hz, 2H).

Example 6

6-fluoro-2-[4-((R)-2-hydroxymethylpyrrolidin-1-ylmethyl)phenyl]-1H-benzimidazole-4-carboxamide The title compound was prepared as the hydrochloride salt using the procedure as described in EXAMPLE 1G, substituting (R)-(+)-pyrrolidin-2-yl-methanol for 2-methylpyrrolidine (72% yield). ¹H NMR (CD₃OD): δ 1.90-1.98 (m, 1H), 1.98-2.06 (m, 1H), 2.12-2.21 (m, 1H), 2.26-2.35 (m, 1H), 3.33-3.40 (m, 1H), 3.43-3.51 (m, 1H), 3.73-3.81 (m, 2H), 3.82-3.89 (m, 1H), 4.44 (d, J=13.1 Hz, 1H), 4.81-4.85 (m, 1H), 7.75 (dd, J=7.8, 2.3 Hz, 1H), 7.88 (d, J=2.1 Hz, 1H), 7.91 (d, J=8.2 Hz, 2H), 8.28 (d, J=8.2 Hz, 2H).

Example 7

2-[4-((S)-2-hydroxymethylpyrrolidin-1-ylmethyl) phenyl]-1H-benzimidazole-4-carboxamide Example 7A 2-(4-diethoxymethylphenyl)-1H-benzimidazole-4-carboxamide The title compound was prepared using the procedure as described in EXAMPLE 1E, substituting 2,3-diaminobenzamide dihydrochloride (synthesized as described in U.S. Pat. No. 6,737,421, column 11, EXAMPLE 2, step (e)) for EXAMPLE 1D (54% yield). MS (DCI/NH₃) m/z 340 (M+H)⁺.

Example 7B 6-fluoro-2-(4-formylphenyl)-1H-benzimidazole-4-carboxamide

The title compound was prepared using the procedure as described in EXAMPLE 1F, substituting EXAMPLE 7A for EXAMPLE 1E (73% yield). MS (DCI/NH₃) m/z 266 (M+H)⁺.

Example 7C

2-[4-((S)-2-hydroxymethylpyrrolidin-1-ylmethyl) phenyl]-1H-benzimidazole-4-carboxamide The title compound was prepared as the hydrochloride salt using the procedure as described in EXAMPLE 1G, substituting (S)-(−)-pyrrolidin-2-ylmethanol for 2-methylpyrrolidine and substituting EXAMPLE 7B for EXAMPLE 1F (7% yield). ¹H NMR (CD₃OD): δ 1.88-2.08 (m, 2H), 2.11-2.23 (m, 1H), 2.25-2.38 (m, 1H), 3.33-3.41 (m, 1H), 3.43-3.54 (m, 1H), 3.75-3.82 (m, 2H), 3.82-3.87 (m, 1H), 4.45 (d, J=13.2 Hz, 1H), 4.84-4.87 (m, 1H), 7.65-7.71 (m, 1H), 7.93 (d, J=8.3 Hz, 2H), 8.00 (d, J=8.3 Hz, 1H), 8.07 (dd, J=7.7, 0.9 Hz, 1H), 8.31 (d, J=8.3 Hz, 2H).

Example 8

2-[4-(2-trifluoromethylpyrrolidin-1-ylmethyl)phenyl]-1H-benzimidazole-4-carboxamide The title compound was prepared as the hydrochloride salt using the procedure as described in EXAMPLE 1G, substituting 2-(trifluoromethyl)pyrrolidine for 2-methylpyrrolidine and EXAMPLE 7B for EXAMPLE 1F (45% yield). ¹H NMR (CD₃OD): δ 2.01-2.11 (m, 1H), 2.12-2.28 (m, 2H), 2.39-2.54 (m, 1H), 3.17-3.27 (m, 1H), 3.39-3.52 (m, 1H), 4.22-4.35 (m, 1H), 4.44 (d, J=13.5 Hz, 1H), 4.63 (d, J=13.8 Hz, 1H), 7.70-7.75 (m, 1H), 7.91 (d, J=8.6 Hz, 2H), 8.03 (dd, J=8.3, 0.92 Hz, 1H), 8.08 (dd, J=7.7, 0.9 Hz, 1H), 8.26 (d, J=8.6 Hz, 2H).

Example 9

2-[4-(2-isopropylpyrrolidin-1-ylmethyl)phenyl]-1H-benzimidazole-4-carboxamide

The title compound was prepared as the hydrochloride salt using the procedure as described in EXAMPLE 1G, substituting 2-isopropylpyrrolidine for 2-methylpyrrolidine and substituting EXAMPLE 7B for EXAMPLE 1F (40% yield). ¹H NMR (CD₃OD): δ 1.06 (d, J=12.9 Hz, 6H), 1.91-2.06 (m, 2H), 2.06-2.22 (m, 2H), 2.22-2.33 (m, 1H), 3.34-3.43 (m, 1H), 3.46-3.54 (m, 1H), 3.54-3.62 (m, 1H), 4.47 (d, J=13.2 Hz, 1H), 4.71 (d, J=12.9 Hz, 1H), 7.70-7.77 (m, 1H), 8.00 (d, J=8.3 Hz, 2H), 8.05 (dd, J=8.3, 0.9 Hz, 1H), 8.09 (dd, J=7.7, 0.9 Hz, 1H), 8.31 (d, J=8.3 Hz, 2H).

Example 10

2-[4-(2-ethylpyrrolidin-1-ylmethyl)phenyl]-1H-benzimidazole-4-carboxamide

The title compound was prepared as the hydrochloride salt using the procedure as described in EXAMPLE 1G, substituting 2-ethylpyrrolidine for 2-methylpyrrolidine and substituting EXAMPLE 7B for EXAMPLE 1F (17% yield). ¹H NMR (CD₃OD): δ 1.03 (t, J=7.4 Hz, 3H), 1.63-1.76 (m, 1H), 1.79-1.91 (m, 1H), 1.94-2.08 (m, 2H), 2.11-2.24 (m, 1H), 2.36-2.51 (m, 1H), 3.34-3.38 (m, 1H), 3.41-3.58 (m, 2H), 4.40 (d, J=13.2 Hz, 1H), 4.76 (d, J=13.2 Hz, 1H), 7.7 (t, J=8.0 Hz, 1H), 7.97 (d, J=8.3 Hz, 2H), 8.04 (dd, J=8.3, 0.6 Hz, 1H), 8.09 (dd, J=7.7, 0.6 Hz, 1H), 8.30 (d, J=8.6 Hz, 2H).

Example 11

2-[4-((R)-2-hydroxymethylpyrrolidin-1-ylmethyl) phenyl]-1H-benzimidazole-4-carboxamide The title compound was prepared as the hydrochloride salt using the procedure as described in EXAMPLE 1G, substituting (R)-(+)-pyrrolidin-2-ylmethanol for 2-methylpyrrolidine and substituting EXAMPLE 7B for EXAMPLE 1F (55% yield). $^1$H NMR (CD$_3$OD): δ 1.90-1.98 (m, 1H), 1.99-2.07 (m, 1H), 2.13-2.23 (m, 1H), 2.27-2.37 (m, 1H), 3.33-3.41 (m, 1H), 3.43-3.52 (m, 1H), 3.76-3.80 (m, 1H), 3.80-3.83 (m, 1H), 3.83-3.88 (m, 1H), 4.47 (d, J=13.1 Hz, 1H), 4.84-4.86 (m, 1H), 7.72 (t, J=7.9 Hz, 1H), 7.95 (d, J=8.2 Hz, 2H), 8.04 (d, J=8.2 Hz, 1H), 8.08 (d, J=7.3 Hz, 1H), 8.30 (d, J=8.2 Hz, 2H).

Example 12

6-chloro-2-[4-(2-trifluoromethylpyrrolidin-1-ylmethyl)phenyl]-1H-benzimidazole-4-carboxamide Example 12A 2-amino-5-chloro-3-nitrobenzamide Step A Preparation of 2-amino-3-nitrobenzamide To a solution of 2-amino-3-nitrobenzoic acid (prepared using the procedure as described in U.S. Pat. No. 6,737,421, EXAMPLE 2, part b) in dimethoxyethane (7.1 mL/g), was added thionyl chloride (1.33 equivalents). The mixture was stirred at 50° C. for 12 hours, cooled and slowly added to concentrated ammonium hydroxide (22 equivalents). The mixture was stirred at 50° C. for 2 hours, water was added, and the mixture was cooled and filtered. The solid was washed with water and isopropanol and dried to give the title compound (89% yield).

Step B

Preparation of 2-amino-5-chloro-3-nitrobenzamide

To a solution of 2-amino-3-nitrobenzamide (4.0 g, 22 mmol) in warm acetonitrile (1250 mL) was added N-chlorosuccinimide (3.1 g, 23 mmol) and the mixture stirred at 60° C. for 20 hours. After cooling, the orange crystalline material was collected by filtration, washed with acetonitrile and dried. The filtrate was concentrated and the solid recrystallized from acetonitrile to provide a second crop of the title compound. (3.98 g, 84%). MS (DCI/NH$_3$) m/z 216 (M+H)$^+$.

Example 12B 2,3-diamino-5-chlorobenzamide

The title compound was prepared using the procedure as described in EXAMPLE 1D, substituting EXAMPLE 12A for EXAMPLE 1C (99% yield). MS (DCI/NH$_3$) M/Z 186 (M+H)$^+$.

Example 12C 6-chloro-2-(4-diethoxymethylphenyl)-1H-benzimidazole-4-carboxamide

The title compound was prepared using the procedure as described in EXAMPLE 1E, substituting EXAMPLE 12B for EXAMPLE 1D (47% yield). MS (DCI/NH$_3$) m/z 374 (M+H)$^+$.

Example 12D 6-chloro-2-(4-formylphenyl)-1H-benzimidazole-4-carboxamide

The title compound was prepared using the procedure as described in EXAMPLE 1F, substituting EXAMPLE 12C for EXAMPLE 1E (82% yield). MS (DCI/NH$_3$) m/z 300 (M+H)$^+$.

Example 12E 6-chloro-2-[4-(2-trifluoromethylpyrrolidin-1-ylmethyl)phenyl]-1H-benzimidazole-4-carboxamide The title compound was prepared as the trifluoroacetic acid salt using the procedure as described in step A of EXAMPLE 1G, substituting 2-(trifluoromethyl)pyrrolidine for 2-methylpyrrolidine, and substituting EXAMPLE 12D for EXAMPLE 1F (28% yield). $^1$H NMR (DMSO-d$_6$): δ 1.72-1.81 (m, 1H), 1.83-1.98 (m, 2H), 2.12-2.25 (m, 1H), 2.64-2.68 (m, 1H), 3.01-3.07 (m, 1H), 3.78-3.84 (m, 1H), 3.97 (d, J=13.4 Hz, 1H), 4.25 (d, J=13.7 Hz, 1H), 7.63 (d, J=7.9 Hz, 2H), 7.84 (s, 1H), 7.85 (s, 1H), 7.97 (br s, 1H), 8.29 (d, J=7.9 Hz, 2H), 9.07 (br s, 1H).

Example 13

6-chloro-2-[4-(2-isopropylpyrrolidin-1-ylmethyl) phenyl]-1H-benzimidazole-4-carboxamide The title compound was prepared as the trifluoroacetic acid salt using the procedure as described in step A of EXAMPLE 1G, substituting 2-isopropylpyrrolidine for 2-methylpyrrolidine, and substituting EXAMPLE 12D for EXAMPLE 1F (8% yield). $^1$H NMR (DMSO-d$_6$): δ 0.92 (d, J=6.9 Hz, 3H), 0.94 (d, J=6.9 Hz, 3H), 1.76-1.83 (m, 1H), 1.83-1.90 (m, 1H), 1.92-2.04 (m, 2H), 2.05-2.15 (m, 1H), 3.18-3.26 (m, 1H), 3.34-3.43 (m, 2H), 4.23-4.62 (m, 2H), 7.82-7.83 (m, 2H), 7.89 (d, J=8.2 Hz, 2H), 7.98 (br s, 1H), 8.38 (d, J=8.2 Hz, 2H), 9.12 (br s, 1H), 10.06 (br s, 1H).

Example 14

6-chloro-2-[4-((S)-2-hydroxymethylpyrrolidin-1-ylmethyl)phenyl]-1H-benzimidazole-4-carboxamide The title compound was prepared as the hydrochloride salt using the procedure as described in EXAMPLE 1G, substituting (S)-(−)-pyrrolidin-2-ylmethanol for 2-methylpyrrolidine and substituting EXAMPLE 12D for EXAMPLE 1F (9% yield). $^1$H NMR (DMSO-d$_6$): δ 1.75-1.91 (m, 2H), 1.95-2.06 (m, 1H), 2.08-2.20 (m, 1H), 3.15-3.23 (m, 1H), 3.27-3.35 (m, 1H), 3.65-3.76 (m, 3H), 4.37 (dd, J=12.9, 6.8 Hz, 1H), 4.67 (dd, J=12.9, 4.3 Hz, 1H), 7.81-7.82 (m, 2H), 7.83-7.85 (m, 2H), 7.94 br (s, 1H), 8.36 (d, J=8.6 Hz, 2H), 9.12 (br s, 1H), 10.29 (br s, 1H).

Example 15

6-chloro-2-[4-((R)-2-hydroxymethylpyrrolidin-1-ylmethyl)phenyl]-1H-benzimidazole-4-carboxamide The title compound was prepared as the hydrochloride salt using the procedure as described in EXAMPLE 1G, substituting (R)-(+)-pyrrolidin-2-ylmethanol for 2-methylpyrrolidine and substituting EXAMPLE 12D for EXAMPLE 1F (24% yield). $^1$H NMR (CD$_3$OD): δ 1.89-1.98 (m, 1H), 1.98-2.06 (m, 1H), 2.12-2.21 (m, 1H), 2.26-2.36 (m, 1H), 3.33-3.40 (m, 1H), 3.43-3.50 (m, 1H), 3.73-3.81 (m, 2H), 3.82-3.88 (m, 1H), 4.44 (d, J=13.1 Hz, 1H), 4.83 (d, J=13.1 Hz, 1H), 7.90 (d, J=8.5 Hz, 2H), 7.98 (d, J=1.8 Hz, 1H), 8.08 (d, J=1.8 Hz, 1H), 8.29 (d, J=8.2 Hz, 2H).

Example 16

2-{4-[2-(2-methylpyrrolidin-1-yl)-ethyl]phenyl}-1H-benzimidazole-4-carboxamide

Example 16A 2-(4-[1,3]-Dioxolan-2-ylmethylphenyl)-1H-benzimidazole-4-carboxamide A solution of 4-(1,3-dioxolan-2-ylmethyl)benzoic acid (1.0 g, 4.80 mmol) in pyridine (5 mL) and N,N-dimethylformamide (5 mL) was treated with 1,1'-carbonyldiimidazole (0.856 g, 5.28 mmol) at 45° C. for 2 hours. 2,3-Diaminobenzamide dihydrochloride (synthesized as described in U.S. Pat. No. 6,737,421, column 11, EXAMPLE 2, step (e), 1.08 g, 4.80 mmol) was added and the mixture stirred at ambient temperature overnight. The mixture was concentrated and the residue heated in acetic acid (30 mL) at 80° C. for 3 hours. After cooling, the mixture was concentrated and the residue partitioned between ethyl acetate and sodium bicarbonate solution. After filtering, the filtrate was concentrated and the residue purified by flash chromatography on silica gel (0-15% methanol in 2:1 ethyl acetate/hexane) to give 1.14 g of the title compound. MS (DCI) m/z 324 (M+H)$^+$.

Example 16B

2-{4-[2-(2-methylpyrrolidin-1-yl)ethyl]phenyl}-1H-benzimidazole-4-carboxamide

A solution of EXAMPLE 16A (750 mg, 2.32 mmol) in acetic acid (30 mL) and water (60 mL) was heated at 70° C. for 18 hours. After cooling, the solution was concentrated to give a light yellow solid. To a solution of the crude aldehyde (170 mg) in N,N-dimethylformamide (1 mL) and methanol (3.5 mL) was added 2-methylpyrrolidine (125 μL, 1.22 mmol) and the mixture stirred at ambient temperature for 1 hour. Sodium cyanoborohydride (77 mg, 1.22 mmol) was added and the mixture heated at 55° C. overnight. The methanol was removed and the residue purified by flash chromatography (silica gel, 1:10:80 ammonium hydroxide/methanol/dichloromethane) followed by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as a trifluoroacetate salt. This material was dissolved in 1:1 methanol/dichloromethane (2 mL) and was treated with a 1M solution of hydrochloric acid in ether (5 mL). Concentration afforded 135 mg of the title compound as the hydrochloride salt. $^1$H NMR (CD$_3$OD) 1.52 (d, J=6.4 Hz, 3H), 1.76-1.85 (m, 1H), 2.07-2.19 (m, 2H), 2.37 (m, 1H), 3.26-3.38 (m, 4H), 3.55-3.61 (m, 1H), 3.66-3.73 (m, 1H), 3.80 (m, 1H), 7.68-7.78 (m, 3H), 8.02 (d, J=8.2 Hz, 1H), 8.07 (d, J=7.6 Hz, 1H), 8.19 (d, J=7.9 Hz, 2H).

Example 17

2-[2-fluoro-4-((S)-2-hydroxymethylpyrrolidin-1-ylmethyl)phenyl]-1H-benzimidazole-4-carboxamide Example 17A methyl 4-cyano-2-fluoro-benzoate A solution of methyl 4-bromo-2-fluorobenzoate (10.0 g, 43 mmol), zinc cyanide (10.0 g, 86 mmol) and palladium tetrakis(triphenylphosphine) (2.5 g, 0.64 mmol) in N,N-dimethylformamide (100 mL) was stirred at 80° C. overnight. After cooling, the mixture was partitioned between ethyl acetate and brine and the organic phase washed with water and concentrated. The residue was purified by flash chromatography on silica gel (1:5 ethyl acetate/hexane) to afford 6.1 g (80%) of the title compound. MS (DCI): m/z 180 (M+H)$^+$.

Example 17B methyl 2-fluoro-4-formyl-benzoate

EXAMPLE 17A (310 mg, 1.73 mmol) was dissolved in 60% aqueous acetic acid (10 mL) with gentle heating. Raney nickel (60 mg) was added and the mixture stirred under hydrogen at ambient temperature for 18 hours. Solid material was filtered off and the filtrate concentrated. The residue was purified by flash chromatography on silica gel (1:4 ethyl acetate/hexane) to give 220 mg (70%) of the title compound. MS (DCI): m/z 183 (M+H)$^+$.

Example 17C methyl 4-[1,3]dioxolan-2-yl-2-fluorobenzoate

A solution of EXAMPLE 17B (2.0 g, 11 mmol), 1,2-ethanediol (1.0 g, 16 mmol), and p-toluenesulfonic acid monohydrate (10 mg) in benzene (10 mL) was heated under reflux with a Dean-Stark apparatus for 6 hours. After cooling, the mixture was partitioned between ethyl acetate and brine and the organic phase washed with 10% sodium hydroxide solution, water and concentrated. The residue was purified by flash chromatography on silica gel (1:5 ethyl acetate/hexane) to give 2.1 g (80%) of the title compound. MS (DCI): m/z 227 (M+H)$^+$.

Example 17D

4-[1,3]dioxolan-2-yl-2-fluorobenzoic acid

To a solution of EXAMPLE 17C (2.0 g) in tetrahydrofuran (10 mL) and water (5 mL) was added a solution of lithium hydroxide monohydrate (1 g) in water (5 mL). Methanol was added until a homogeneous solution formed. The solution was stirred at ambient temperature for 4 hours and concentrated to 5 mL. This was acidified with 2N hydrochloric acid to pH 2 and partitioned between ethyl acetate and water. The organic phase was washed with water, dried over magnesium sulfate, filtered and concentrated to give 1.5 g (79%) of the title compound. MS (DCI): m/z 213 (M+H)$^+$.

Example 17E 2-(4-[1,3]dioxolan-2-yl-2-fluorophenyl)-1H-benzimidazole-4-carboxamide A solution of EXAMPLE 17D (1.5 g, 7.1 mmol) in pyridine (5 mL) and N,N-dimethylformamide (20 mL) was treated with 1,1'-carbonyldiimidazole (1.4 g, 8.5 mmol) at 40° C. for 30 minutes. 2,3-Diaminobenzamide dihydrochloride (synthesized as described in U.S. Pat. No. 6,737,421, column 11, EXAMPLE 2, step (e), 1.58 g, 7.1 mmol) was added and the mixture stirred at ambient temperature overnight. Solvents were removed and the residue was stirred in acetic acid (10 mL) at 80° C. overnight. After concentration, the residue was purified by flash chromatography on silica gel (ethyl acetate) to give 500 mg (22%) of the title compound. MS (DCI/NH$_3$) m/z 329 (M+H)$^+$.

Example 17F 2-(2-fluoro-4-formylphenyl)-1H-benzimidazole-4-carboxamide

A solution of EXAMPLE 17E (500 mg, 1.5 mmol) in acetic acid (5 mL) and water (10 mL) was heated at 70° C. overnight. After cooling, the mixture was concentrated to give 400 mg (94%) of the title compound. MS (DCI/NH$_3$) m/z 285 (M+H)$^+$.

Example 17G

2-[2-fluoro-4-((S)-2-hydroxymethylpyrrolidin-1-ylmethyl)phenyl]-1H-benzimidazole-4-carboxamide To a solution of EXAMPLE 17F (70 mg, 0.25 mmol) in N,N-dimethylformamide (2 mL) and methanol (4 mL) was added (S)-pyrrolidin-2-ylmethanol (37 mg, 0.37 mmol) and the solution stirred at ambient temperature for 10 minutes. Sodium cyanoborohydride (38 mg) was added and the mixture heated at 55° C. overnight. After cooling, the mixture was concentrated and the residue purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide 65 mg of the title compound as a trifluoroacetic acid salt. $^1$H NMR (CD$_3$OD): δ 1.87-2.07 (m, 2H); 2.15 (d, J=4.0 Hz, 1H); 2.30 (dd, J=12.5, 6.41 Hz, 1H); 3.25-3.38 (m, 1H); 3.50 (s, 1H); 3.77 (d, J=7.3 Hz, 2H); 3.87 (d, J=7.6 Hz, 1H); 4.35 (d, J=12.8 Hz, 1H); 4.75 (d, J=13.1 Hz, 1H); 7.42 (s, 1H); 7.55 (s, 2H); 7.82 (s, 1H); 7.97 (s, 1H); 8.39 (d, J=1.2 Hz, 1H).

Example 18

2-{4-[(3-aminopyrrolidin-1-yl)methyl]phenyl}-1H-benzimidazole-4-carboxamide

Example 18A tert-butyl 1-{4-[4-(aminocarbonyl)-1H-benzimidazol-2-yl]benzyl}pyrrolidin-3-ylcarbamate A solution of EXAMPLE 7B (300 mg, 1.13 mmol) and 3-(tert-butoxycarbonylamino)pyrrolidine (631 mg, 3.39 mmol) in 1:1 methanol/N,N'-dimethylformamide (20 mL) was stirred at ambient temperature for 2 hours. Sodium cyanoborohydride (213 mg, 3.39 mmol) and zinc chloride (154 mg, 1.13 mmol) were added and the mixture stirred at 50° C. for 18 hours. The mixture was concentrated and the residue purified by HPLC (Zorbax C-8, 0.1% trifluoroacetic acid/acetonitrile/water) to provide the title compound (415 mg, 84%). MS (DCI/NH$_3$) m/z 436 (M+H)$^+$.

Example 18B

2-{4-[(3-aminopyrrolidin-1-yl)methyl]phenyl}-1H-benzimidazole-4-carboxamide

A solution of EXAMPLE 18A (410 mg, 0.94 mmol) in dichloromethane (40 mL) was treated with trifluoroacetic acid (15 mL) at 0° C. and the mixture stirred at ambient temperature for 3 hours. The solution was diluted with acetonitrile and concentrated to provide the title compound as a trifluoroacetate salt (300 mg, 96%). $^1$H NMR (CD$_3$OD) δ 2.17-2.29 (m, 1H), 2.59-2.71 (m, 1H), 3.43-3.51 (m, 1H), 3.56 (dd, J=12.7, 4.4 Hz, 1H), 3.64-3.73 (m, 1H), 3.80 (dd, J=12.8, 8.2 Hz, 1H), 4.14-4.24 (m, 1H), 4.55 (d, J=5.5 Hz, 2H), 7.45 (t, J=7.8 Hz, 1H), 7.77 (d, J=8.5 Hz, 2H), 7.81 (dd, J=7.9, 0.9 Hz, 1H), 7.98 (dd, J=7.6, 0.9 Hz, 1H), 8.30 (d, J=8.2 Hz, 2H).

Example 19

2-(4-{[3-(dimethylamino)pyrrolidin-1-yl]methyl}phenyl)-1H-benzimidazole-4-carboxamide A solution of EXAMPLE 18B (50 mg, 0.15 mmol), triethylamine (52 μL, 0.37 mmol) and formaldehyde (37% in water, 8 μL, 0.30 mmol) in 1:1 methanol/N,N'-dimethylformamide (6 mL) was stirred at ambient temperature for 2 hours. Sodium cyanoborohydride (28 mg, 0.45 mmol) and zinc chloride (20 mg, 0.15 mmol) were added and the mixture stirred at 50° C. for 18 hours. The mixture was concentrated and the residue purified by HPLC (Zorbax C-8, 0.1% trifluoroacetic acid/acetonitrile/water) to provide the trifluoroacetate salt of the title compound. The hydrochloride salt (18 mg, 33%) was obtained by treatment of a methanol solution of the purified trifluoroacetate salt with a solution of hydrochloric acid in ether. $^1$H NMR (CD$_3$OD) δ 2.46-2.59 (m, 1H), 2.63-2.76 (m, 1H), 2.99 (s, 6H), 3.53-3.65 (m, 1H), 3.70-3.83 (m, 1H), 3.92-4.08 (m, 2H), 4.23-4.38 (m, 1H), 4.73 (s, 2H), 7.69-7.75 (m, 1H), 8.03 (dd, J=8.3, 0.9 Hz, 3H), 8.08 (dd, J=7.5, 0.8 Hz, 1H), 8.30 (d, J=8.6 Hz, 2H).

Example 20

2-(4-{[3-(isopropylamino)pyrrolidin-1-yl]methyl}phenyl)-1H-benzimidazole-4-carboxamide The title compound as the hydrochloride salt was prepared according to the procedure for EXAMPLE 19, substituting acetone for formaldehyde (26% yield). $^1$H NMR (CD$_3$OD): δ 1.40 (d, J=6.4 Hz, 6H), 2.31-2.51 (m, 1H), 2.69-2.85 (m, 1H), 3.45-3.57 (m, 2H), 3.76-3.84 (m, 2H), 3.85-3.94 (m, 1H), 4.31-4.48 (m, 1H), 4.73 (s, 2H), 7.66-7.72 (m, 1H), 7.99-8.03 (m, 3H), 8.07 (dd, J=7.7, 0.9 Hz, 1H), 8.29 (d, J=8.6 Hz, 2H).

Example 21

2-[4-({3-[(cyclopropylmethyl)amino]pyrrolidin-1-yl}methyl)phenyl]-1H-benzimidazole-4-carboxamide The title compound as the hydrochloride salt was prepared according to the procedure for EXAMPLE 19, substituting cyclopropanecarboxaldehyde for formaldehyde. (24% yield). $^1$H NMR (CD$_3$OD) δ 0.40-0.54 (m, 2H), 0.73 (d, J=8.0

Hz, 2H), 1.09-1.22 (m, 1H), 2.33-2.47 (m, 1H), 2.65-2.86 (m, 1H), 3.00 (d, J=7.36 Hz, 2H), 3.41-3.56 (m, 1H), 3.73-3.85 (m, 2H), 3.88-4.03 (m, 1H), 4.17-4.36 (m, 1H), 4.71 (s, 2H), 7.69 (t, J=7.8 Hz, 1H), 8.00 (d, J=8.0 Hz, 3H), 8.07 (d, J=7.7 Hz, 1H), 8.30 (d, J=8.3 Hz, 2H).

Example 22

2-(4-{[3-(cyclobutylamino)pyrrolidin-1-yl]methyl}phenyl)-1H-benzimidazole-4-carboxamide The title compound as the hydrochloride salt was prepared according to the procedure for EXAMPLE 19, substituting cyclobutanone for formaldehyde (31% yield). $^1$H NMR (CD$_3$OD) δ 1.86-2.02 (m, 2H), 2.25-2.44 (m, 5H), 2.58-2.78 (m, 1H), 3.46-3.63 (m, 1H), 3.71-3.82 (m, 2H), 3.84-3.95 (m, 2H), 4.10-4.22 (m, 1H), 4.71 (s, 2H), 7.64-7.70 (m, 1H), 7.99 (d, J=8.3 Hz, 3H), 8.06 (dd, J=7.5, 0.8 Hz, 1H), 8.30 (d, J=8.3 Hz, 2H).

Example 23

2-(4-{[3-(dicyclobutylamino)pyrrolidin-1-yl]methyl}phenyl)-1H-benzimidazole-4-carboxamide The title compound as the hydrochloride salt was prepared according to the procedure for EXAMPLE 19, substituting cyclobutanone for formaldehyde (14% yield). $^1$H NMR (CD$_3$OD): δ 1.75-1.92 (m, 4H), 2.30-2.44 (m, 4H), 2.44-2.59 (m, 6H), 3.39-3.50 (m, 1H), 3.60-3.71 (m, 1H), 3.76-3.88 (m, 2H), 3.96-4.06 (m, 3H), 4.27-4.43 (m, 1H), 4.65-4.71 (m, 2H), 7.67 (t, J=8.0 Hz, 1H), 7.99 (d, J=7.4 Hz, 1H), 8.00 (d, J=8.0 Hz, 2H), 8.07 (d, J=6.8 Hz, 1H), 8.29 (d, J=8.6 Hz, 2H);

Example 24

2-(4-{[2-(aminomethyl)pyrrolidin-1-yl]methyl}phenyl)-1H-benzimidazole-4-carboxamide Example 24A tert-butyl (1-{4-[4-(aminocarbonyl)-1H-benzimidazol-2-yl]benzyl}pyrrolidin-2-yl)methylcarbamate The title compound was prepared according to the procedure for EXAMPLE 18A, substituting tert-butyl pyrrolidin-2-ylmethylcarbamate for 3-(tert-butoxycarbonylamino)pyrrolidine. (85% yield). MS (DCI/NH$_3$) m/z 450 (M+H)$^+$.

Example 24B 2-(4-{[2-(aminomethyl)pyrrolidin-1-yl]methyl}phenyl)-1H-benzimidazole-4-carboxamide The title compound as the trifluoroacetate salt was prepared according to the procedure for EXAMPLE 18B, substituting EXAMPLE 24A for EXAMPLE 18A. (94% yield). $^1$H NMR (CD$_3$OD): δ 1.97-2.11 (m, 2H), 2.12-2.23 (m, 1H), 2.41-2.53 (m, 1H), 3.24-3.29 (m, 1H), 3.33-3.37 (m, 1H), 3.43-3.55 (m, 1H), 3.79-3.89 (m, 1H), 4.35 (d, J=12.9 Hz, 1H), 4.70 (d, J=12.9 Hz, 1H), 7.46 (t, J=7.8 Hz, 1H), 7.79 (d, J=8.3 Hz, 2H), 7.83 (d, J=7.4 Hz, 1H), 7.99 (dd, J=7.7, 0.9 Hz, 1H), 8.30 (d, J=8.3 Hz, 2H).

Example 25

2-[4-({2-[(dimethylamino)methyl]pyrrolidin-1-yl}methyl)phenyl]-1H-benzimidazole-4-carboxamide The title compound as the hydrochloride salt was prepared according to the procedure for EXAMPLE 19, substituting EXAMPLE 24B for EXAMPLE 18B. (27% yield). $^1$H NMR (CD$_3$OD): δ 2.08-2.21 (m, 2H), 2.23-2.34 (m, 1H), 2.59-2.72 (m, 1H), 3.04 (s, 6H), 3.34-3.51 (m, 2H), 3.72 (dd, J=13.4, 8.8 Hz, 1H), 3.99 (dd, J=13.5, 4.3 Hz, 1H), 4.18-4.30 (m, 1H), 4.42-4.53 (m, 1H), 4.99 (d, J=9.5 Hz, 1H), 7.66-7.71 (m, 1H), 8.00 (dd, J=8.3, 0.9 Hz, 1H), 8.06 (d, J=4.0 Hz, 1H), 8.06-8.09 (m, 2H), 8.30 (d, J=8.3 Hz, 2H).

Example 26

2-{4-[(2-{[(cyclopropylmethyl)amino]methyl}pyrrolidin-1-yl)methyl]phenyl}-1H-benzimidazole-4-carboxamide The title compound as the hydrochloride salt was prepared according to the procedure for EXAMPLE 19 substituting cyclopropane carboxaldehyde for formaldehyde and EXAMPLE 24B for EXAMPLE 18B (14% yield). $^1$H NMR (CD$_3$OD): δ 0.46-0.56 (m, 2H), 0.71-0.79 (m, 2H), 1.14-1.29 (m, 1H), 2.16 (d, J=6.4 Hz, 2H), 2.20-2.30 (m, 1H), 2.53-2.65 (m, 1H), 2.99-3.16 (m, 2H), 3.34-3.41 (m, 1H), 3.43-3.50 (m, 1H), 3.62 (dd, J=13.4, 7.5 Hz, 1H), 3.78 (dd, J=13.5, 4.6 Hz, 1H), 4.07-4.20 (m, 1H), 4.47 (d, J=12.6 Hz, 1H), 4.99 (d, J=12.9 Hz, 1H), 7.65-7.71 (m, 1H), 8.00 (dd, J=8.3, 0.9 Hz, 1H), 8.07 (dd, J=7.5, 0.8 Hz, 3H), 8.29 (d, J=8.3 Hz, 2H).

Example 27

2-[4-({2-[(dicyclobutylamino)methyl]pyrrolidin-1-yl}methyl)phenyl]-1H-benzimidazole-4-carboxamide The title compound as the hydrochloride salt was prepared according to the procedure for EXAMPLE 19 substituting cyclobutanone for formaldehyde and EXAMPLE 24B for EXAMPLE 18B (39% yield). $^1$H NMR (CD$_3$OD): δ 1.77-1.98 (m, 4H), 2.09-2.20 (m, 2H), 2.23-2.30 (m, 1H), 2.36 (d, J=2.2 Hz, 4H), 2.45-2.60 (m, 4H), 2.72-2.83 (m, 1H), 3.33-3.45 (m, 2H), 3.65 (dd, J=13.7, 10.3 Hz, 1H), 3.84 (dd, J=13.8, 3.1 Hz, 1H), 3.90-4.01 (m, 2H), 4.08-4.19 (m, 1H), 4.48 (d, J=12.9 Hz, 1H), 4.99 (d, J=12.0 Hz, 1H), 7.66-7.71 (m, 1H), 8.00 (dd, J=8.3, 0.9 Hz, 1H), 8.03-8.09 (m, 3H), 8.29 (d, J=8.3 Hz, 2H).

Example 28

2-[4-({2-[(isopropylamino)methyl]pyrrolidin-1-yl}methyl)phenyl]-1H-benzimidazole-4-carboxamide The title compound as the hydrochloride salt was prepared according to the procedure for EXAMPLE 19 substituting acetone for formaldehyde and EXAMPLE 24B for EXAMPLE 18B (27% yield). $^1$H NMR (CD$_3$OD): δ 1.43 (d, J=6.4 Hz, 6H), 2.09-2.19 (m, 2H), 2.20-2.30 (m, 1H), 2.50-2.62 (m, 1H), 3.35-3.42 (m, 1H), 3.43-3.50 (m, 1H), 3.51-3.57 (m, 1H), 3.60 (dd, J=13.2, 7.7 Hz, 1H), 3.69-3.78 (m, 1H), 4.06-4.14 (m, 1H), 4.46 (d, J=13.5 Hz, 1H), 4.99 (d, J=13.2 Hz, 1H), 7.68 (t, J=8.0 Hz, 1H), 7.99 (d, J=8.0 Hz, 1H), 8.07 (d, J=7.7 Hz, 3H), 8.29 (d, J=8.3 Hz, 2H).

Example 29

2-(4-{[(2S,5S)-2,5-bis(methoxymethyl)pyrrolidin-1-yl]methyl}phenyl)-1H-benzimidazole-4-carboxamide To a solution of EXAMPLE 7B (75 mg, 0.28 mmol) in N,N'-dimethylformamide (4 mL) and methanol (4 mL) was added (S,S)-(+)-2,5-bis(methoxymethyl)pyrrolidine (134 mg, 0.84 mmol) and the mixture stirred at ambient temperature for 1.5 hours. Sodium cyanoborohydride (53 mg, 0.28 mmol) was added and the mixture heated at 55° C. overnight. After cooling, the mixture was concentrated and the residue purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt. Dissolution in methanol and treatment with a 1M hydrochloric acid solution in ether, followed by concentration, afforded the title compound as the hydrochloride salt (20 mg, 18%). $^1$H NMR (CD$_3$OD) δ 1.91-1.99 (m, 1H), 2.13-2.19 (m, 1H), 2.18-2.26 (m, 1H), 2.32-2.40 (m, 1H), 3.22 (s, 3H), 3.23-3.27 (m, 1H), 3.45-3.51 (m, 1H), 3.49 (s, 3H), 3.78-3.83 (m, 1H), 3.87-3.93 (m, 1H), 3.99 (m, 1H), 4.07-4.13 (m, 1H), 4.52 (d, J=13.4 Hz, 1H), 4.71 (d, J=13.7 Hz, 1H), 7.66 (t, J=7.9 Hz, 1H), 7.95 (d, J=8.2 Hz, 2H), 7.99 (d, J=8.2 Hz, 1H), 8.06 (d, J=7.6 Hz, 1H), 8.31 (d, J=8.2 Hz, 2H).

Example 30

2-{2-fluoro-4-[(2-methylpyrrolidin-1-yl)methyl]phenyl}-1H-benzimidazole-4-carboxamide To a suspension of EXAMPLE 17F (50 mg, 0.17 mmol) in methanol (10 mL) was added 2-methylpyrrolidine (43 mg, 0.5 mmol) and the mixture stirred at 50° C. until complete dissolution. Sodium cyanoborohydride (38 mg) was added and the mixture heated at 55° C. overnight. After cooling, the mixture was concentrated and the residue purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt (44 mg). $^1$H NMR (DMSO-D6) δ 1.39 (d, J=6.4 Hz, 3H); 1.59-1.74 (m, 1H); 1.84-1.93 (m, 1H); 1.95-2.09 (m, 1H); 2.18-2.38 (m, 1H); 3.18-3.29 (m, 1H); 3.30-3.44 (m, 1H); 3.48-3.63 (m, 1H); 4.29 (dd, J=12.9, 7.1 Hz, 1H); 4.67 (dd, J=13.2, 2.5 Hz, 1H); 7.40 (t, J=8.3 Hz, 1H); 7.61 (dd, J=8.3, 1.53 Hz, 1H); 7.72 (d, J=12.0 Hz, 1H); 7.78 (d, J=8.3 Hz, 1H); 7.84 (d, J=1.5 Hz 1H); 7.92 (d, J=8.0 Hz 1H); 8.40 (t, J=8.0 Hz, 1H); 9.15 (s, 1H); 9.98 (s, 1H).

Example 31

2-(4-{[3-(dimethylamino)pyrrolidin-1-yl]methyl}-2-fluorophenyl)-1H-benzimidazole-4-carboxamide The title compound was prepared as the trifluoroacetate salt according to the procedure for EXAMPLE 30, substituting 3-dimethylaminopyrrolidine for 2-methylpyrrolidine. $^1$H NMR (DMSO-D$_6$) δ 2.05-2.26 (m, 1H); 2.29-2.43 (m, 1H); 2.83 (s, 6H); 3.20-3.31 (m, 1H); 3.33-3.49 (m, 2H); 3.65 (dd, J=12.6, 8.3 Hz, 1H); 3.92-4.11 (m, 2H); 4.26 (m, 1H); 7.39 (t, J=8.0 Hz, 1H); 7.52 (d, J=8.0 Hz, 1H); 7.59 (d, J=111.7 Hz, 1H); 7.78 (d, J=1.8 Hz, 1H); 7.83 (d, J=7.1 Hz, 1H); 7.92 (d, J=7.1 Hz, 1H); 8.35 (t, J=8.0 Hz, 1H); 9.20 (s, 1H); 9.65 (s, 1H).

Example 32

2-{4-[(3-aminopyrrolidin-1-yl)methyl]-2-fluorophenyl}-1H-benzimidazole-4-carboxamide To a solution of EXAMPLE 17F (100 mg, 0.3 mmol) in N,N'-dimethylformamide (5 mL) and methanol (10 mL) was added tert-butyl pyrrolidin-3-yl-carbamate (111 mg, 0.6 mmol) and the mixture stirred at ambient temperature for 10 minutes. Sodium cyanoborohydride (38 mg) was added and the mixture heated at 55° C. overnight. After cooling, the mixture was concentrated and the residue was treated with dichloromethane (4 mL) and trifluoroacetic acid (1 mL) for 1 hour and concentrated. The residue was purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt (79 mg). $^1$H NMR (DMSO-D$_6$) δ 2.02-2.17 (m, 1H); 2.35-2.48 (m, 1H); 3.40 (s, 2H); 3.46-3.61 (m, 1H); 3.64-3.82 (m, 1H); 3.92-4.12 (m, 1H); 4.45-4.62 (m, 2H); 7.41 (t, J=7.7 Hz, 1H); 7.59 (dd, J=8.0, 1.2 Hz, 1H); 7.68 (d, J=12.0 Hz, 1H); 7.78 (s, 1H); 7.84 (d, J=8.0 Hz, 1H); 7.93 (d, J=8.3 Hz, 1H); 8.27-8.52 (m, J=7.8, 7.8 Hz, 2H); 9.16 (s, 1H).

Example 33

2-(2-fluoro-4-{[(2R)-2-(hydroxymethyl)pyrrolidin-1-yl]methyl}phenyl)-1H-benzimidazole-4-carboxamide The title compound was prepared as trifluoroacetate salt according to the procedure for EXAMPLE 30, substituting (R)-2-hydroxymethylpyrrolidine for 2-methylpyrrolidine. $^1$H NMR (DMSO-D$_6$) δ 1.75-1.83 (m, 1H), 1.82-1.90 (m, 1H), 1.98-2.05 (m, 1H), 2.12-2.21 (m, 1H), 3.21-3.28 (m, 1H), 3.34-3.40 (m, 1H), 3.65 (m, 2H), 4.41 (d, J=12.8 Hz, 1H), 4.67 (d, J=12.8 Hz, 1H), 7.40 (t, J=7.8 Hz, 1H), 7.61 (d, J=7.9 Hz, 1H), 7.71 (d, J=11.9 Hz, 1H), 7.81 (br s, 1H), 7.83 (d, J=7.9 Hz, 1H), 7.92 (d, J=7.3 Hz, 1H), 8.40 (t, J=7.8 Hz, 1H), 9.15 (br s, 1H), 9.74 (br s, 1H).

Example 34

2-[4-(1-pyrrolidin-1-ylethyl)phenyl]-1H-benzimidazole-4-carboxamide

Example 34A 2-(4-acetylphenyl)-1H-benzimidazole-4-carboxamide

4-Acetylbenzoic acid (1.64 g, 10 mmol) in N,N-dimethylformamide (10 mL) and pyridine (10 mL) was stirred at 40° C. for 10 minutes. 1,1'-carbonyldiimidazole (1.7 g, 10.5 mmol) was added and the mixture was stirred at 40° C. for 30 minutes. 2,3-diaminobenzamide dihydrochloride (synthesized as described in U.S. Pat. No. 6,737,421, 2.2 g, 10 mmol) was added and the mixture was stirred at ambient temperature for 2.5 hours. Isopropyl alcohol (20 mL) was added and the mixture was stirred at ambient temperature for 20 hours. The resulting solid was filtered, washed with isopropyl alcohol and dried to give 2.1 g of a yellow solid. The crude material was stirred in water (30 mL) with 50% sodium hydroxide (1 mL) at ambient temperature for 7.5 hours. The solution was filtered and the solid (1.84 g) collected and stirred in refluxing acetic acid (25 mL) for 4 hours. The mixture was concentrated, stirred in dichloromethane, filtered, and dried to give the title compound (1.78 g, 64%). $^1$H NMR (DMSO-d$_6$) δ 9.27 (br, 1H), 8.40 (d, J=8.4 Hz, 2H), 8.16 (d, J=8.5 Hz, 2H), 7.89 (d, J=7.5 Hz, 1H), 7.78 (d, J=6.8 Hz, 1H), 7.78 (br, 1H), 7.37 (t, J=7.8 Hz, 1H), 2.66 (s, 3H).

Example 34B

2-[4-(1-pyrrolidin-1-ylethyl)phenyl]-1H-benzimidazole-4-carboxamide

A solution of EXAMPLE 34A (0.1 g, 0.4 mmol) and pyrrolidine (0.13 mL, 1.6 mmol) in methanol (1 mL) was treated with sodium cyanoborohydride (0.05 g, 0.8 mmol) and acetic acid (0.2 mL) and the mixture stirred overnight at 70° C. The residue was concentrated and purified by flash chromatography on silica gel using 0-10% dichloromethane/methanol/0.1% ammonium hydroxide to provide the title compound, which was dissolved in methanol (1 mL), treated with a solution of 1M hydrochloric acid in ether (2 mL) and stirred at ambient temperature for 2 hours. The precipitate was filtered to give the title compound as the hydrochloride salt. $^1$H NMR (DMSO-d$_6$) δ 11.26 (s, 1H), 8.34 (d, J=8.4 Hz, 2H), 7.85-7.91 (m, 3H), 7.79 (d, J=7.2 Hz, 2H), 7.39 (t, J=7.8 Hz, 1H), 4.51 (qd, J=7.4, 7.2 Hz, 1H), 3.70 (dd, J=11.4, 4.5 Hz, 1H), 3.12-3.20 (m, 1 Hz), 2.95-3.02 (m, 1H), 2.89 (dq, J=11.2, 8.1 Hz, 1H), 1.91-2.00 (m, 2H), 1.79-1.88 (m, 1H), 1.69 (d, J=6.9 Hz, 3H).

Example 35

2-{4-[1-(4-methyl-[1,4]diazepan-1-yl)ethyl]phenyl}-1H-benzimidazole-4-carboxamide The title compound as the hydrochloride salt was prepared as described in EXAMPLE 34B by substituting 1-methyl-[1,4]diazepane for pyrrolidine. $^1$H NMR (DMSO-d$_6$) δ 11.42 (s, 1H) 9.70 (s, 1H), 8.37 (d, J=7.5 Hz, 2H), 7.84-7.92 (m, 3H), 7.79 (d, J=8.1 Hz, 2H), 7.38 (t, J=7.8 Hz, 1H), 3.64 (s, 1H), 3.51-3.58 (m, 3H), 3.48 (s, 1H), 3.17 (s, 4H), 2.73-2.80 (m, 5H), 2.11-2.20 (m, 3H).

Example 36

2-[4-(1-(azepan-1-yl-ethyl)phenyl]-1H-benzimidazole-4-carboxamide

The title compound as the hydrochloride salt was prepared as described in EXAMPLE 34B by substituting azepane for pyrrolidine. $^1$H NMR (DMSO-d$_6$) δ 8.71 (s, 1H), 8.34 (d, J=8.4 Hz, 2H), 7.85-7.90 (m, 3H), 7.72-7.79 (m, 2H), 7.37 (t, J=7.8 Hz, 1H), 4.65-4.70 (m, 1H) 3.51 (s, 1H), 3.02-3.06 (m, 5H), 2.96 (d, J=6.2 Hz, 2H), 1.73-1.83 (m, 4H), 1.47-1.67 (m, 4H).

Example 37

2-[4-(1-(morpholin-4-ylethyl)phenyl]-1H-benzimidazole-4-carboxamide

The title compound was prepared as described in EXAMPLE 34B by substituting morpholine for pyrrolidine. The product was purified by HPLC on a C18 column using 0-100% acetonitrile/water/0.1% trifluoroacetic acid to provide the title compound as the trifluoroacetate salt. $^1$H NMR (DMSO-d$_6$) δ 9.24 (s, 1H), 8.36 (d, J=8.2 Hz, 2H), 7.89 (d, J=7.6 Hz, 1H), 7.72-7.81 (m, 4H), 7.38 (t, J=7.6 Hz, 1H), 4.61 (d, J=7.6 Hz 1H) 3.60-3.77 (m, 5H), 2.94-3.02 (m 3 Hz), 1.71 (d, J=7.0 Hz, 4H).

Example 38

2-{4-[1-(4-methyl-piperazin-1-yl)ethyl]phenyl}-1H-benzimidazole-4-carboxamide

The title compound was prepared as described in EXAMPLE 34B by substituting 1-methylpiperazine for pyrrolidine. The product was purified by HPLC on a C18 column using 0-100% acetonitrile/water/0.1% trifluoroacetic acid to provide the title compound as the trifluoroacetate salt. $^1$H NMR (DMSO-d$_6$) δ 9.25 (s, 1H), 8.26 (d, J=8.2 Hz, 2H), 7.88 (d, J=6.7 Hz, 1H), 7.73-7.81 (m, 2H), 7.59 (d, J=8.2 Hz, 2H), 7.36 (t, J=7.8 Hz, 1H), 3.75-3.82 (m, 4H), 3.36-3.42 (m, 1H), 3.31 (s, 1H), 3.03 (s, 1H), 2.78 (s, 3H), 2.40 (s, 1H), 1.45 (d, J=6.7 Hz, 3H), 1.03-1.11 (m, 1H).

Example 39

2-{4-[1-(4-isopropylpiperazin-1-yl)ethyl]phenyl}-1H-benzimidazole-4-carboxamide

The title compound was prepared as described in EXAMPLE 34B by substituting 1-isopropylpiperazine for pyrrolidine. The product was purified by HPLC on a C18 column using 0-100% acetonitrile/water/0.1% trifluoroacetic acid to provide the title compound as the trifluoroacetate salt. $^1$H NMR (DMSO-d$_6$) δ 9.25 (s, 1H), 8.27 (d, J=8.2 Hz, 2H), 7.88 (d, J=7.6 Hz, 1H), 7.73-7.80 (m, 2H), 7.61 (d, J=8.2 Hz, 2H), 7.37 (t, J=7.8 Hz, 1H), 3.42-3.49 (m, 2H), 3.38 (dd, J=14.0, 7.0 Hz, 3H), 3.07 (s, 3 Hz), 2.41 (s, 1H), 1.48 (d, J=6.7 Hz, 3H), 1.18-1.24 (m, 6H).

Example 40

2-[4-(1-methyl-1-pyrrolidin-1-ylethyl)phenyl]-1H-benzimidazole-4-carboxamide

Example 40A (4-bromophenyl)pyrrolidin-1-ylmethanone

A solution of 4-bromobenzoyl chloride (3 g, 13.7 mmol)) in dichloromethane (25 mL) was cooled to 0° C. and treated with pyrrolidine (2.5 mL, 30.3 mmol) and triethylamine (2 mL, 14.4 mmol). The mixture was warmed to ambient temperature over 3 hours and concentrated. The residue was purified by flash chromatography on silica gel using 10-60% hexane/ethyl acetate to provide the title compound (3.1 g, 89%). MS (ESI) m/e 256 (M+H)$^+$.

Example 40B

1-[1-(4-bromophenyl)-1-methylethyl]pyrrolidine

A solution of EXAMPLE 40A (0.5 g, 2 mmol)) in tetrahydrofuran (5 mL) was cooled to −15° C. and treated with zirconium(IV) chloride (0.46 g, 2 mmol). The mixture was stirred at −15° C. for 30 minutes and a 3M solution of methylmagnesium bromide in ether (4 mL, 12 mmol) was slowly added. The mixture was warmed to ambient temperature overnight then cooled to 0° C. 25% sodium hydroxide was added, the mixture extracted with dichloromethane, and the organic layer separated, washed with water and brine, and concentrated. The residue was purified by flash chromatography on silica gel using 10-60% hexane/ethyl acetate to give the title compound (0.2 g, 38%). MS (ESI) m/e 270 (M+H)$^+$.

Example 40C 4-(1-methyl-1-pyrrolidin-1-ylethyl)benzaldehyde

A solution of EXAMPLE 40B (0.4 g, 1.5 mmol)) in tetrahydrofuran (5 mL) was cooled to −78° C. and treated with a 1.3 M solution of sec-butyl lithium in cyclohexane (1.8 mL, 2.3 mmol). The mixture was stirred for 30 minutes at −78° C. and treated with N,N'-dimethylformamide (0.4 mL, 5.2 mmol). The mixture was warmed to ambient temperature over 1.5 hours, acetic acid (1 mL) added and the mixture stirred at ambient temperature for 10 minutes. Water (2 mL) was added and the mixture diluted with ethyl acetate. The organic layer was separated, washed with saturated sodium bicarbonate, water and brine, and concentrated. The residue was purified by flash chromatography on silica gel using 10-60% hexane/ethyl acetate to give the title compound (0.135 g, 42%). MS (ESI) m/e 218 (M+H)$^+$.

Example 40D

2-[4-(1-methyl-1-pyrrolidin-1-ylethyl)phenyl]-1H-benzimidazole-4-carboxamide

A solution of 2,3-diamino-benzamide dihydrochloride (0.134 g, 0.6 mmol) (2.2 g, 10 mmol) and EXAMPLE 40C (0.13 g, 0.6 mmol) in methanol (4 mL) was treated with 10% palladium on carbon (0.04 g). The mixture was refluxed overnight, filtered through celite and concentrated. The residue was purified by flash chromatography on silica gel using 0-10% dichloromethane/methanol/0.1% ammonium hydroxide to provide the title compound. $^1$H NMR (DMSO-d$_6$) δ 9.12 (s, 1H), 8.36 (d, J=8.5 Hz, 2H), 8.06 (d, J=8.5 Hz, 2H), 7.90 (d, J=7.3 Hz, 1H), 7.75-7.84 (m, 2H), 7.40 (t, J=7.8 Hz, 1H), 3.39 (s, 1H), 3.17 (s, 2H), 1.82-1.88 (m, 4H), 1.81 (s, 6H) 1.72 (s, 1H), 1.09 (t, J=6.9 Hz, 1H).

Example 41

2-[5-(1-morpholin-4-ylethyl)thiophen-2-yl]-1H-benzimidazole-4-carboxamide

Example 41A 5-acetylthiophene-2-carboxylic acid (2-amino-3-carbamoylphenyl)amide A solution of 5-acetylthiophene-2-carboxylic acid (1.80 g, 10.55 mmol) in pyridine (12 mL) and N,N'-dimethylformamide (12 mL) was treated with 1,1'-carbonyldiimidazole (1.88 g, 11.60 mmol) at 45° C. for 4 hours. 2,3-Diaminobenzamide dihydrochloride (2.36 g, 10.55 mmol) was added and the mixture stirred at ambient temperature overnight. The mixture was concentrated and the residue stirred in ethyl acetate and water, filtered, and the yellow solid washed with water and ethyl acetate and dried to give the title compound (2.91 g, 91%). MS(APCI): 304 (M+1)$^+$.

Example 41B 2-(5-acetylthiophen-2-yl)-1H-benzimidazole-4-carboxamide

To a solution of EXAMPLE 41A (1.70 g) in hot N,N'-dimethylformamide (60 mL) was added acetic acid (50 mL) and the solution heated at 125° C. for 3 hours. After cooling, the solution was filtered, and the yellow solid washed with methanol and dried to give the title compound (1.52 g, 95%). MS (APCI): 286 (M+1)$^+$.

Example 41C

2-[5-(1-morpholin-4-ylethyl)thiophen-2-yl]-1H-benzimidazole-4-carboxamide

A solution of EXAMPLE 41B (100 mg, 0.35 mmol) and morpholine (61 μL, 0.70 mmol) in dimethylsulfoxide (3 mL) was stirred at ambient temperature overnight. Zinc chloride (48 mg, 0.35 mmol) was added and the mixture stirred at ambient temperature for 1 hour. Sodium cyanoborohydride (44 mg, 0.70 mmol) and methanol (3 mL) were added and the suspension heated at 80° C. for 2 days. After cooling, solvent was removed and the residue purified by HPLC (Zorbax, C-18, 250×2.54 column, Mobile phase A: 0.1% trifluoroacetic acid in water; B: 0.1% trifluoroacetic acid in acetonitrile; 0-100% gradient) to provide the title compound as the trifluoroacetate salt (77.6 mg, 34%). $^1$H NMR (CD$_3$OD): δ 1.89 (d, J=7.2 Hz, 3H), 3.23-3.33 (m, 4H), 3.82-4.06 (m, 4H), 4.93 (q, J=7.0 Hz, 1H), 7.39 (t, J=7.8 Hz, 1H), 7.46 (d, J=3.7 Hz, 1H), 7.74 (d, J=8.1 Hz, 1H), 7.85 (d, J=3.7 Hz, 1H), 7.96 (d, J=7.8 Hz, 1H).

Example 42

2-(2-fluoro-4-{[(2S)-2-(methoxymethyl)pyrrolidin-1-yl]methyl}phenyl)-1H-benzimidazole-4-carboxamide The title compound was prepared as the trifluoroacetate salt according to the procedure for Example 17G, substituting (S)-(+)-2-(methoxymethyl)pyrrolidine for (S)-pyrrolidin-2-ylmethanol. $^1$H NMR (CD$_3$OD) δ 1.86-1.96 (m, 1H), 1.96-2.09 (m, 1H), 2.11-2.22 (m, 1H), 2.32 (dd, J=13.1, 6.7 Hz, 1H), 3.34-3.36 (m, 1H), 3.44 (s, 3H), 3.47-3.55 (m, 1H), 3.64 (s, 2H), 3.87 (d, J=4.9 Hz, 1H), 4.38 (d, J=13.1 Hz, 1H), 4.71 (d, J=13.1 Hz, 1H), 7.44 (t, J=7.93 Hz, 1H), 7.53-7.60 (m, 2H), 7.85 (d, J=7.6 Hz, 1H), 8.00 (d, J=6.7 Hz, 1H), 8.45 (t, J=7.9 Hz, 1H).

Example 43

2-(2-fluoro-4-{[(2R)-2-(methoxymethyl)pyrrolidin-1-yl]methyl}phenyl)-1H-benzimidazole-4-carboxamide The title compound was prepared as the trifluoroacetate salt according to the procedure for Example 17G, substituting (R)-(−)-2-(methoxymethyl)pyrrolidine for (S)-pyrrolidin-2-ylmethanol. $^1$H NMR (CD$_3$OD) δ 1.86-1.96 (m, 1H) 1.96-2.09 (m, 1H) 2.11-2.22 (m, 1H) 2.32 (dd, J=13.1, 6.7 Hz, 1H) 3.34-3.36 (m, 1H) 3.44 (s, 3H) 3.47-3.55 (m, 1H), 3.64 (s, 2H), 3.87 (d, J=4.9 Hz, 1H), 4.38 (d, J=13.1 Hz, 1H), 4.71 (d, J=13.1 Hz, 1H), 7.44 (t, J=7.9 Hz, 1H), 7.53-7.60 (m, 2H), 7.85 (d, J=7.6 Hz, 1H), 8.00 (d, J=6.7 Hz, 1H), 8.45 (t, J=7.9 Hz, 1H).

What is claimed is:
1. A compound of Formula (I)

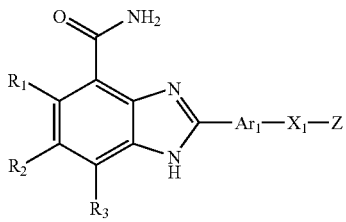

Formula (I)

or a therapeutically acceptable salt thereof, wherein
$R_1$, $R_2$, and $R_3$ are independently selected from the group consisting of hydrogen, and halogen;
$Ar_1$ is aryl, wherein $Ar_1$ is optionally substituted with halogen;
$X_1$ is alkylenyl;
Z is heterocycle, wherein Z is substituted with 1, 2, 3, or 4 substituents selected from the group consisting of alkoxyalkyl, haloalkyl, hydroxyalkyl, $NR_CR_D$, and $NR_CR_D$alkyl; and
$R_C$ and $R_D$ are independently selected from the group consisting of hydrogen, alkyl, cycloalkyl, and cycloalkylalkyl.

2. The compound according to claim 1, wherein $Ar_1$ is phenyl.

3. The compound according to claim 1, wherein Z is pyrrolidinyl, wherein the pyrrolidinyl is substituted with 1, 2, 3, or 4 substituents selected from the group consisting of alkoxyalkyl, haloalkyl, hydroxyalkyl, $NR_CR_D$, and $NR_CR_D$alkyl; and
$R_C$ and $R_D$ are independently selected from the group consisting of hydrogen, alkyl, cycloalkyl, and cycloalkylalkyl.

4. The compound according to claim 1, wherein Z is pyrrolidinyl substituted with $NR_CR_D$.

5. The compound according to claim 1, wherein Z is pyrrolidinyl substituted with $NR_CR_D$alkyl.

6. The compound according to claim 1, wherein Z is pyrrolidinyl substituted with hydroxyalkyl.

7. The compound according to claim 1, wherein $Ar_1$ is phenyl and Z is pyrrolidinyl, wherein the pyrrolidinyl is substituted with 1, 2, 3, or 4 substituents selected from the group consisting of alkoxyalkyl, haloalkyl, hydroxyalkyl, $NR_CR_D$, and $NR_CR_D$alkyl; and
$R_C$ and $R_D$ are independently selected from the group consisting of hydrogen, alkyl, cycloalkyl, and cycloalkylalkyl.

8. The compound according to claim 1, wherein $Ar_1$ is phenyl substituted with halogen.

9. The compound according to claim 1, wherein $R_1$, $R_2$, and $R_3$ are hydrogen.

10. The compound according to claim 1 selected from the group consisting of
6-fluoro-2-[4-((S)-2-hydroxymethylpyrrolidin-1-ylmethyl)phenyl]-1H-benzimidazole-4-carboxamide;
6-fluoro-2-[4-(2-trifluoromethylpyrrolidin-1-ylmethyl)phenyl]-1H-benzimidazole-4-carboxamide;
6-fluoro-2-[4-((R)-2-hydroxymethylpyrrolidin-1-ylmethyl)phenyl]-1H-benzimidazole-4-carboxamide;
2-[4-((S)-2-hydroxymethylpyrrolidin-1-ylmethyl)phenyl]-1H-benzimidazole-4-carboxamide;
2-[4-(2-trifluoromethylpyrrolidin-1-ylmethyl)phenyl]-1H-benzimidazole-4-carboxamide;
2-[4-((R)-2-hydroxymethylpyrrolidin-1-ylmethyl)phenyl]-1H-benzimidazole-4-carboxamide;
6-chloro-2-[4-(2-trifluoromethylpyrrolidin-1-ylmethyl)phenyl]-1H-benzimidazole-4-carboxamide;
6-chloro-2-[4-((S)-2-hydroxymethylpyrrolidin-1-ylmethyl)phenyl]-1H-benzimidazole-4-carboxamide;
6-chloro-2-[4-((R)-2-hydroxymethylpyrrolidin-1-ylmethyl)phenyl]-1H-benzimidazole-4-carboxamide;
2-[2-fluoro-4-((S)-2-hydroxymethylpyrrolidin-1-ylmethyl)phenyl]-1H-benzimidazole-4-carboxamide;
2-{4-[(3-aminopyrrolidin-1-yl)methyl]phenyl}-1H-benzimidazole-4-carboxamide;
2-(4-{[3-(dimethylamino)pyrrolidin-1-yl]methyl}phenyl)-1H-benzimidazole-4-carboxamide;
2-(4-{[3-(isopropylamino)pyrrolidin-1-yl]methyl}phenyl)-1H-benzimidazole-4-carboxamide;
2-[4-({3-[(cyclopropylmethyl)amino]pyrrolidin-1-yl}methyl)phenyl]-1H-benzimidazole-4-carboxamide;
2-(4-{[3-(cyclobutylamino)pyrrolidin-1-yl]methyl}phenyl)-1H-benzimidazole-4-carboxamide;
2-(4-{[3-(dicyclobutylamino)pyrrolidin-1-yl]methyl}phenyl)-1H-benzimidazole-4-carboxamide;
2-(4-{[2-(aminomethyl)pyrrolidin-1-yl]methyl}phenyl)-1H-benzimidazole-4-carboxamide;
2-[4-({2-[(dimethylamino)methyl]pyrrolidin-1-yl}methyl)phenyl]-1H-benzimidazole-4-carboxamide;
2-{4-[(2-{[(cyclopropylmethyl)amino]methyl}pyrrolidin-1-yl)methyl]phenyl}-1H-benzimidazole-4-carboxamide;
2-[4-({2-[(dicyclobutylamino)methyl]pyrrolidin-1-yl}methyl)phenyl]-1H-benzimidazole-4-carboxamide;
2-[4-({2-[(isopropylamino)methyl]pyrrolidin-1-yl}methyl)phenyl]-1H-benzimidazole-4-carboxamide;
2-(4-{[(2S,5S)-2,5-bis(methoxymethyl)pyrrolidin-1-yl]methyl}phenyl)-1H-benzimidazole-4-carboxamide;
2-(4-{[3-(dimethylamino)pyrrolidin-1-yl]methyl}-2-fluorophenyl)-1H-benzimidazole-4-carboxamide;
2-{4-[(3-aminopyrrolidin-1-yl)methyl]-2-fluorophenyl}-1H-benzimidazole-4-carboxamide;
2-(2-fluoro-4-{[(2R)-2-(hydroxymethyl)pyrrolidin-1-yl]methyl}phenyl)-1H-benzimidazole-4-carboxamide;
2-(2-fluoro-4-{[(2S)-2-(methoxymethyl)pyrrolidin-1-yl]methyl}phenyl)-1H-benzimidazole-4-carboxamide; and
2-(2-fluoro-4-{[(2R)-2-(methoxymethyl)pyrrolidin-1-yl]methyl}phenyl)-1H-benzimidazole-4-carboxamide.

11. A pharmaceutical composition comprising a compound of Formula (I) of claim 1, or a therapeutically acceptable salt thereof, in combination with a therapeutically acceptable carrier.

* * * * *

UNITED STATES PATENT AND TRADEMARK OFFICE
CERTIFICATE OF CORRECTION

| | | |
|---|---|---|
| PATENT NO. | : 7,999,117 B2 | Page 1 of 1 |
| APPLICATION NO. | : 12/413834 | |
| DATED | : August 16, 2011 | |
| INVENTOR(S) | : Giranda et al. | |

It is certified that error appears in the above-identified patent and that said Letters Patent is hereby corrected as shown below:

Front Page, Item (73) Assignee to read as --Abbott Laboratories, Abbott Park, IL--

Signed and Sealed this
Twenty-second Day of January, 2013

David J. Kappos
*Director of the United States Patent and Trademark Office*